United States Patent
Zheng et al.

(10) Patent No.: US 12,099,049 B2
(45) Date of Patent: Sep. 24, 2024

(54) METHOD AND DEVICE FOR DETECTING HOOK EFFECT IN TURBIDIMETRIC INHIBITION IMMUNOASSAY, AND COMPUTER READABLE MEDIUM

(71) Applicant: Shenzhen Mindray Bio-Medical Electronics Co., Ltd., Shenzhen (CN)

(72) Inventors: Wenbo Zheng, Shenzhen (CN); Bo Ye, Shenzhen (CN); Wentao Wei, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 320 days.

(21) Appl. No.: 17/686,250

(22) Filed: Mar. 3, 2022

(65) Prior Publication Data

US 2022/0187278 A1    Jun. 16, 2022

Related U.S. Application Data

(63) Continuation of application No. PCT/CN2019/104452, filed on Sep. 4, 2019.

(51) Int. Cl.
*G01N 33/49* (2006.01)
*G01N 1/40* (2006.01)

(52) U.S. Cl.
CPC ........... *G01N 33/49* (2013.01); *G01N 1/4044* (2013.01)

(58) Field of Classification Search
CPC ..... G01N 1/405; G01N 33/49; G01N 21/3103
See application file for complete search history.

(56) References Cited

U.S. PATENT DOCUMENTS

| 6,044,330 A | 3/2000 | Patzke | |
| 2014/0186972 A1* | 7/2014 | Campbell | G01N 33/5438 422/69 |

FOREIGN PATENT DOCUMENTS

| CN | 104991056 A | | 10/2015 | |
| CN | 105190311 A | | 12/2015 | |
| CN | 105339794 A | * | 2/2016 | ......... G01N 33/5306 |
| CN | 105466927 A | | 4/2016 | |
| CN | 107422134 A | | 12/2017 | |
| CN | 107703132 A | | 2/2018 | |
| CN | 110082345 A | | 8/2019 | |
| CN | 110542662 A | * | 12/2019 | |
| EP | 2790019 A1 | | 10/2014 | |
| JP | 2019120581 | | 7/2019 | |
| WO | WO-2018204784 A1 | * | 11/2018 | .............. B01L 3/502 |
| WO | WO-2020068574 A1 | * | 4/2020 | ........... G01N 21/272 |

* cited by examiner

*Primary Examiner* — Maurice C Smith
(74) *Attorney, Agent, or Firm* — Kory Christensen

(57) ABSTRACT

Provided are a method and device for recognizing hook effect in immune turbidimetry, and a computer readable medium. This method generates a reaction curve using light signals measured in a predetermined time period by immune reaction of analyte in a sample, and uses distribution information of the reaction curve in the predetermined time period to determine whether the sample has hook effect. This method only uses measurement information of a small predetermined time period in entire reaction time to determine whether a sample has hook effect, and terminates the test in time, thus accelerating the speed of immune turbidimetry detection of samples with hook effect.

20 Claims, 10 Drawing Sheets

METHOD AND DEVICE FOR DETECTING HOOK EFFECT IN TURBIDIMETRIC INHIBITION IMMUNOASSAY, AND COMPUTER READABLE MEDIUM

CROSS-REFERENCE TO RELATED APPLICATIONS

This application is a continuation of International Application No. PCT/CN2019/104452, filed Sep. 4, 2019, the content of which is incorporated herein by reference.

TECHNICAL FIELD

The disclosure relates to technologies for sample testing using turbidimetric inhibition immunoassay, and in particular to a method, apparatus, and computer-readable medium for detecting hook effect caused by an excessively high concentration of a protein to be tested in a sample.

BACKGROUND

In biochemical immunoassay, low test results or even false negatives are often caused by an inappropriate proportion of antigen to antibody. Taking an excess of antigen as an example, when the amount of antibody-antigen precipitation is plotted against the amount of antigen, a phenomenon that a hook (HOOK) curve (A) deviating from a normal curve (B) occurs at the end of the increased antigen amount is called hook effect (see FIG. 1). Hook effect is due to soluble complexes appearing when the amount of antigen or antibody to be tested is greatly excessive, resulting in deviation of test results.

Turbidimetric inhibition immunoassay is a dynamic assay based on binding of antigen to antibody. The turbidimetric inhibition immunoassay includes turbidimetric immunoassay and nephelometric immunoassay. Antibody-antigen complexes scatter and block light. Therefore, the amount of antibody-antigen complexes is proportional to change in intensity of transmitted or scattered light. When the amount of antibody is constant, change of light intensity is also proportional to antigen content. Under certain conditions, antigen content in a sample can be obtained by detecting change in intensity of transmitted light or scattered light.

When the concentration of antibody is constant, the amount of formed immune complex increases as the amount of antigen increases in test sample, and the turbidity of the reaction solution also increases accordingly. However, when the amount of analyte (i.e., antigen) in a sample is too large, hook effect occurs, that is, low test results or even false negatives occur.

At present, turbidimetric inhibition immunoassay is widely used in fully automated biochemistry analyzers. In order to obtain accurate test results, it is required to detect hook effect caused by an excessively high concentration of analyte in a sample, and then the sample with hook effect is properly diluted and tested again to obtain a correct test result. For example, Chinese Patent Application No. CN 105339794 A discloses a method of detecting and analyzing light signals after entire reaction time by using two specific wavelengths, and then calculating a reaction rate to determine whether a sample has hook effect. This method requires simultaneous detection using two wavelengths, and the determination can be made only after the sample is completely tested.

Blood biochemical tests, such as C-reactive protein (CRP), serum amyloid A (SAA), etc., are widely used in clinical testing. Especially in seasons of high incidence of respiratory diseases, C-reactive protein often needs to be tested in addition to the routine blood test for whole blood, so that a physician can make a correct clinical diagnosis. The C-reactive protein test often takes longer than the routine blood test, and therefore a patient needs to wait longer for all test results. If a sample has hook effect, retesting is required, and the patient waits even longer for the test results. Therefore, there is a need to quickly detect whether a sample has hook effect, so as to quickly obtain correct test results.

SUMMARY

An objective of the disclosure is to propose a method for detecting hook effect in turbidimetric inhibition immunoassay, so as to obtain a determination result more quickly and shorten test time of samples with hook effect.

To this end, according to a first aspect of the disclosure, a method for detecting hook effect in turbidimetric inhibition immunoassay is provided. The method includes:
   a) after a sample is mixed with a reaction reagent so that an analyte in the sample starts to react, obtaining a measured value $A_i$ at a time point $T_i$ within a predetermined time period $T_i$ to $T_n$ after the reaction starts, where i is an integer from 1 to n, so that a plurality of measured values $A_1$ to $A_n$ are obtained to generate a reaction curve for the time period;
   b) estimating a concentration $C_e$ of the analyte based on the reaction curve for the time period;
   c) obtaining, according to the estimated concentration $C_e$ of the analyte, a pre-stored reference curve corresponding to the concentration; and
   d) comparing distribution information of the reaction curve for the predetermined time period with distribution information of the reference curve for the corresponding time period to determine whether the sample has hook effect.

According to an implementation, in step a) of the method, $T_n$ is smaller than or equal to a time point $T_{90}$ at which the reaction proceeds to 90% of an entire reaction time, preferably $T_n$ is smaller than or equal to a time point $T_{70}$ at which the reaction proceeds to 70% of the entire reaction time, and more preferably $T_n$ is smaller than or equal to a time $T_{50}$ at which the reaction proceeds to 50% of the entire reaction time.

Alternatively, in step a) of the method, $T_n$ is smaller than or equal to a corresponding time point at which a slope trend of the reference curve changes.

According to an implementation, the predetermined time period accounts for 10% to 70%, preferably 15% to 50%, or more preferably 15% to 40% of the entire reaction time.

According to a specific implementation, the time period for generating the reaction curve of the analyte is a time period from start of the reaction to completion of 10% to 70%, preferably 10% to 50%, more preferably 10% to 40% of the reaction. That is, the reaction curve of the analyte is obtained by using the measured values detected during the first 10% to 70%, preferably the first 10% to 50%, or more preferably the first 10% to 40% of the reaction.

According to an implementation, the distribution information in the method may comprise at least one of a measured value feature, a reaction rate feature, and a reaction acceleration feature.

According to the disclosure, if a difference between the distribution information of the reaction curve and the distribution information of the reference curve conforms to a predetermined feature, it is determined that the sample has hook effect, and the testing is terminated.

According to an implementation, the step of comparing distribution information of the reaction curve for the predetermined time period with distribution information of the reference curve for the corresponding time period includes: comparing the measured values of the reaction curve for the predetermined time period with measured values of the reference curve for the corresponding time period.

According to another implementation, the step of comparing distribution information of the reaction curve for the predetermined time period with distribution information of the reference curve for the corresponding time period includes: performing first derivation on the reaction curve and the reference curve respectively to obtain a reaction rate curve and a reference rate curve, and comparing the reaction rate curve with the reference rate curve.

According to still another implementation, the step of comparing distribution information of the reaction curve for the predetermined time period with distribution information of the reference curve for the corresponding time period includes: performing second derivation on the reaction curve and the reference curve respectively to obtain a reaction acceleration curve and a reference acceleration curve, and comparing the reaction acceleration curve with the reference acceleration curve.

According to an implementation, the step of comparing distribution information of the reaction curve for the predetermined time period with distribution information of the reference curve for the corresponding time period includes: comparing values of respective distribution information of the reaction curve and the reference curve at a same reaction time point, and/or comparing average values of a plurality of pieces of respective distribution information of the reaction curve and the reference curve in a same time period.

According to a specific implementation, in step d), the measured value $A_i$ of the reaction curve at the time point $T_i$ and a reference value $A_{i(f)}$ of the reference curve at a corresponding time point are substituted into the following formula to obtain a reaction difference $\delta_i$ %:

$$\delta_i \% = [(A_i - A_{i(f)})/A_{i(f)}] \times 100\%$$

when $\delta_i$ % is greater than or equal to a predetermined threshold $\delta 1$, it is determined that the sample has hook effect, or an average measured value $\overline{A}$ of the reaction curve within the time period $T_1$ to $T_n$ and an average reference value $\overline{A}_{(f)}$ of the reference curve within the corresponding time period are substituted into the following formula to obtain an average reaction difference $\Delta$ % for the time period:

$$\Delta \% = [(\overline{A} - \overline{A}_{(f)})/\overline{A}_{(f)}] \times 100\%$$

when $\Delta$ % is greater than or equal to a predetermined threshold $\Delta 1$, it is determined that the sample has hook effect.

In a specific implementation, alternatively, in step d), the measured value $A_i$ of the reaction curve at the time point $T_i$ and a reference value $A_{i(f)}$ of the reference curve at a corresponding time point are substituted into the following formula to obtain a reaction difference $\delta_i$ %:

$$\delta_i \% = [(A_1 - A_{i(f)})/A_{i(f)}] \times 100\%$$

when $\delta_i$ % is greater than or equal to a predetermined threshold $\delta 2$, it is determined that the sample has hook effect, and an average measured value $\overline{A}$ of the reaction curve within the time period $T_1$ to $T_n$ and an average reference value $\overline{A}_{(f)}$ of the reference curve within the corresponding time period are substituted into the following formula to obtain an average reaction difference $\Delta$ % for the time period:

$$\Delta \% = [(\overline{A} - \overline{A}_{(f)})/\overline{A}_{(f)}] \times 100\%$$

when $\Delta$ % is greater than or equal to a predetermined threshold $\Delta 2$, it is determined that the sample has hook effect.

According to another specific implementation, step d) includes:

performing first derivation the reaction curve $A=f(T)$ and the reference curve $A_{(f)}=f(T_{(f)})$ respectively with respect to time to obtain curves of reaction rate as a function of time $v=A'=f'(T)$ and $v'=A_{(f)}'=f'(T_{(f)})$; and a reaction rate value $v_i$ at the time point $T_i$ and a reference reaction rate value $v_{i(f)}$ at a corresponding time point are substituted into the following formula to obtain a reaction rate difference $\delta v_i$ %:

$$\delta v_i \% = (|v_i - v_{i(f)}|/v_{i(f)}) \times 100\%$$

when $\delta v_i$ % is greater than or equal to a predetermined threshold $\delta v1$, it is determined that the sample has hook effect, or an average reaction rate value $\overline{v}$ within the time period $T_1$ to $T_n$ and an average reference reaction rate value $\overline{v}_{(f)}$ within the corresponding time period are substituted into the following formula to obtain an average reaction rate difference $\Delta v$ % for the time period:

$$\Delta v \% = (|\overline{v} - \overline{v}_{(f)}|/\overline{v}_{(f)}) \times 100\%$$

when $\Delta v$ % is greater than or equal to a predetermined threshold $\Delta v1$, it is determined that the sample has hook effect.

In a specific implementation, alternatively, step d) includes:

performing first derivation on the reaction curve $A=f(T)$ and the reference curve $A_{(f)}=f(T_{(f)})$ respectively with respect to time to obtain curves of reaction rate as a function of time $v=A'=f'(T)$ and $v'=A_{(f)}'=f'(T_{(f)})$; and a reaction rate value $v_i$ at the time point $T_i$ and a reference reaction rate value $v_{i(f)}$ at a corresponding time point are substituted into the following formula to obtain a reaction rate difference $\delta v_i$ %:

$$\delta v_i \% = (|v_i - v_{i(f)}|/v_{i(f)}) \times 100\%$$

when $\delta v_i$ % is greater than or equal to a predetermined threshold $\delta v2$, it is determined that the sample has hook effect, and an average reaction rate value $\overline{v}$ within the time period $T_1$ to $T_n$ and an average reference reaction rate value $\overline{v}_{(f)}$ within the corresponding time period are substituted into the following formula to obtain an average reaction rate difference $\Delta v$ % for the time period:

$$\Delta v \% = (|\overline{v} - \overline{v}_{(f)}|/\overline{v}_{(f)}) \times 100\%$$

when $\Delta v$ % is greater than or equal to a predetermined threshold $\Delta v2$, it is determined that the sample has hook effect.

In the embodiments in which the first derivation is performed, the actual reaction rate curve and the reference reaction rate curve may approach or intersect with each other. In this case, an area where they approach or intersect with each other and nearby areas may be avoided to select the time point for determining whether there is hook effect to calculate $\delta v_i$ %. In a specific embodiment, $T_n$ is smaller than a time point at which the difference $\delta v_i$ % is approximately zero.

In a specific embodiment, alternatively, the above step d) includes:

performing first derivation on the reaction curve $A=f(T)$ and the reference curve $A_{(f)}=f(T_{(f)})$ respectively with respect to time to obtain curves of reaction rate as a function of time $v=A'=f'(T)$ and $v'=A_{(f)}'=f'(T_{(f)})$; and it is determined that the sample has hook effect when the reaction rate curve $v=A'=f'(T)$ has an overall trend that the reaction rate decreases over time within the time period of $T_1$ to $T_n$, and the reference reaction rate curve $v'=A_{(f)}'=f'(T_{(f)})$ has an overall trend that the reference reaction rate increases first and then decreases over time within the corresponding time period.

According to yet another specific embodiment, the above step d) includes:

performing second derivation the reaction curve $A=f(T)$ and the reference curve $A_{(f)}=f(T_{(f)})$ respectively to obtain curves of reaction acceleration as a function of time $a=A''=f''(T)$ and $a_{(f)}=A_{(f)}''=f''(T_{(f)})$; and a reaction acceleration value $a_i$ at the time point $T_i$ and a reference reaction acceleration value $a_{(f)}$ at a corresponding time point are substituted into the following formula to obtain a reaction acceleration difference $\delta a_i$ %:

$$\delta a_i \% = |(a_i - a_{i(f)})/a_{i(f)}| \times 100\%$$

When $\delta a_i$ % is greater than or equal to a predetermined threshold $\delta a1$, it is determined that the sample has hook effect, or an average reaction acceleration value $\bar{a}$, within the time period $T_1$ to $T_n$ and an average reference reaction acceleration value $\bar{a}_{(f)}$ within the corresponding time period are substituted into the following formula to obtain an average reaction acceleration difference $\Delta a$ % for the time period:

$$\Delta a \% = |(\bar{a} - \bar{a}_{(f)})/\bar{a}_{(f)}| \times 100\%$$

When $\Delta a$ % is greater than or equal to a predetermined threshold $\Delta a1$, it is determined that the sample has hook effect.

In a specific embodiment, alternatively, the above step d) includes:

performing second derivation the reaction curve $A=f(T)$ and the reference curve $A_{(f)}=f(T_{(f)})$ respectively to obtain curves of reaction acceleration as a function of time $a=A''=f''(T)$ and $a_{(f)}=A_{(f)}''=f''(T_{(f)})$; and a reaction acceleration value $a_i$ at the time point $T_i$ and a reference reaction acceleration value $a_{i(f)}$ at a corresponding time point are substituted into the following formula to obtain a reaction acceleration difference $\delta a_i$ %:

$$\delta a_i \% = |(a_i - a_{i(f)})/a_{i(f)}| \times 100\%$$

When $\delta a_i$ % is greater than or equal to a predetermined threshold $\delta a2$, it is determined that the sample has hook effect, and an average reaction acceleration value $\bar{a}_i$ within the time period $T_1$ to $T_n$ and an average reference reaction acceleration value $\bar{a}_{(f)}$ within the corresponding time period are substituted into the following formula to obtain an average reaction acceleration difference $\Delta a$ % for the time period:

$$\Delta a \% = |(\bar{a} - \bar{a}_{(f)})/\bar{a}_{(f)}| \times 100\%$$

When $\Delta a$ % is greater than or equal to a predetermined threshold $\Delta a2$, it is determined that the sample has hook effect.

In an embodiment, $T_n$ is smaller than or equal to a time point when the reference reaction acceleration reaches a substantially constant value $a_{f const}$.

In the above-mentioned specific embodiments of performing the second derivation, the actual reaction acceleration and the reference reaction acceleration may tend to approach each other after a time period of reaction, and in some cases may intersect. When selecting the time point for comparing the difference, the time point within the time period before the two acceleration values approach each other can be selected according to experience.

In a specific embodiment, alternatively, step d) includes:

performing second derivation the reaction curve $A=f(T)$ and the reference curve $A_{(f)}=f(T_{(f)})$ respectively to obtain curves of reaction acceleration as a function of time $a=A''=f''(T)$ and $a_{(f)}=A_{(f)}''=f''(T_{(f)})$; and it is determined that the sample has hook effect, when within the time period of $T_1$ to $T_n$, the reaction acceleration curve $a=A''=f''(T)$ has an overall trend that the reaction acceleration increases over time and the reference reaction acceleration curve $a_{(f)}=A_{(f)}''=f''(T_{(f)})$ has an overall trend that the reference reaction acceleration decreases over time.

Further, according to a first aspect of the disclosure, also provided is a method for detecting hook effect in turbidimetric inhibition immunoassay, wherein the method includes:

a') after a sample is mixed with a reaction reagent so that an analyte in the sample starts to react, obtaining a measured value $A_i$ at a time point $T_i$ within a predetermined time period $T_1$ to $T_n$ after the reaction starts, where i is an integer from 1 to n, so that a plurality of measured values $A_1$ to $A_n$ are obtained to generate a reaction curve for the time period;

b') performing derivation the reaction curve $A=f(T)$ within the time period with respect to time T, and determining whether the sample has hook effect according to a contour of the curve after the derivation.

According to an embodiment, in step a'), $T_n$ is smaller than or equal to a time point $T_{90}$ when the reaction proceeds to 90% of an entire reaction time, preferably L is smaller than or equal to a time point $T_{70}$ when the reaction proceeds to 70% of the entire reaction time, more preferably $T_n$ is smaller than or equal to a time point $T_{50}$ when the reaction proceeds to 50% of the entire reaction time.

According to an embodiment, the predetermined time period accounts for 10% to 70%, preferably 15% to 50%, more preferably 15% to 40% of the entire reaction time.

According to a specific implementation, the predetermined time period for generating the reaction curve of the analyte is a time period from initiation of the reaction to completion of 10% to 70%, preferably 10% to 50%, more preferably 10% to 40% of the reaction.

In an embodiment, the derivation is first derivation or second derivation.

According to a specific embodiment, in step b'), first derivation is performed on the reaction curve $A=f(T)$ with respect to time T to obtain a curve of reaction rate as a function of time $v=A'=f'(T)$, and it is determined that the sample has hook effect when the reaction rate curve $v=A'=f'(T)$ has an overall trend that the reaction rate decreases over time within the time period of $T_1$ to $T_n$.

According to another specific embodiment, in step b'), second derivation is performed on the reaction curve $A=f(T)$ with respect to time T to obtain a curve of reaction acceleration as a function of time $a=A''=f''(T)$, and it is determined that the sample has hook effect when the reaction acceleration curve $a=A''=f''(T)$ has an overall trend that the reaction acceleration increases over time within the time period of $T_1$ to $T_n$.

According to the method for detecting hook effect of the disclosure, if the contour of the curve after derivation conforms to a predetermined feature, it is determined that the sample has hook effect, and the testing is terminated.

In the methods of the disclosure, the sample is a mammal whole blood sample, preferably a human whole blood sample.

The analyte in the sample of the disclosure is a protein, preferably C-reactive protein or serum amyloid A protein.

Before step a) or a'), the methods of the disclosure further include a step of aspirating the sample into a reaction chamber, and adding the reaction reagent for mixing, wherein the sample reacts with the reagent, so that red blood cells in the sample are lysed.

In the methods, the reaction reagent includes a substance that can specifically react with the analyte, preferably a latex coated with the substance that can specifically react with the analyte.

According to an embodiment, before the step a) or a'), the sample is divided into at least two equal parts, where one part is subjected to routine blood test, and the other part is subjected to the test of the analyte and subjected to the steps of the aforementioned method.

According to a second aspect of the disclosure, a blood analysis system is provided, including:

a sampling portion configured to obtain a blood sample and transfer the blood sample to a reaction portion;

a reagent supply portion configured to store a first reaction reagent and supply the first reaction reagent to the reaction portion as needed;

the reaction portion including a first reaction chamber and configured to mix the blood sample with the first reaction reagent to prepare a first test solution;

a detection system including a light source and a detector for testing the first test solution and configured to obtain measured values of the test solution;

a controller, which is coupled to the sampling portion, the reagent supply portion, the reaction portion and the detection system, and is configured to control actions of the sampling portion, the reagent supply portion, the reaction portion and the detection system;

a processor, which is coupled to the detection system, the processor is configured to: obtain, from the detection system, a measured value $A_i$ at a time point $T_i$ within a predetermined time period $T_1$ to $T_n$ after the reaction starts, where i is an integer from 1 to n, so that a plurality of measured values $A_1$ to $A_n$ are obtained to generate a reaction curve for the time period; estimate a concentration $C_e$ of the analyte based on the reaction curve for the time period and a pre-stored calibration curve; obtain a pre-stored reference curve corresponding to the concentration according to the estimated concentration $C_e$ of the analyte; and compare distribution information of the reaction curve for the predetermined time period with distribution information of the reference curve for the corresponding time period, to determine whether the sample has hook effect, alternatively, the processor is configured to: obtain, from the detection system, a measured value $A_i$ at a time point $T_i$ within a time period $T_1$ to $T_n$ after the reaction starts, where i is an integer from 1 to n, so that a plurality of measured values $A_1$ to $A_n$ are obtained to generate a reaction curve for the time period; and perform derivation on the reaction curve $A=f(T)$ within the time period with respect to time T, and determine whether the sample has hook effect based on a contour of the curve after the derivation, and output a determination result to the controller.

According to an embodiment, the step of comparing the distribution information of the reaction curve for the predetermined time period with the distribution information of the reference curve for the corresponding time period performed by the processor includes: comparing the measured values of the reaction curve for the predetermined time period with measured values of the reference curve for the corresponding time period.

According to another embodiment, the step of comparing the distribution information of the reaction curve for the predetermined time period with the distribution information of the reference curve for the corresponding time period performed by the processor includes: performing first derivation on the reaction curve and the reference curve respectively to obtain a reaction rate curve and a reference rate curve, and comparing the reaction rate curve with the reference rate curve.

According to yet another embodiment, the step of comparing the distribution information of the reaction curve for the predetermined time period with the distribution information of the reference curve for the corresponding time period performed by the processor includes: performing second derivation on the reaction curve and the reference curve respectively to obtain a reaction acceleration curve and a reference acceleration curve, and comparing the reaction acceleration curve with the reference acceleration curve.

According to a specific embodiment, the step of comparing the distribution information of the reaction curve for the predetermined time period with the distribution information of the reference curve for the corresponding time period performed by the processor includes: comparing values of respective distribution information of the reaction curve and the reference curve at a same reaction time point, and/or comparing the average values of a plurality of pieces of respective distribution information of the reaction curve and the reference curve within a same time period.

In the blood analysis system of the disclosure, the controller is further configured to:

control the detection system to stop testing when receiving a result that the current test sample has hook effect;

control the sampling portion to obtain the sample again and transfer the obtained sample to the first reaction chamber of the reaction portion;

control the reagent supply portion to supply the first reaction reagent to the first reaction chamber to prepare a second test solution, where a dilution factor of the sample in the second test solution is greater than a dilution factor of the sample in the first test solution; and control the detection system to test the second test solution.

Examples of detectors may include photometers, in particular turbidimeters and/or nephelometers.

In the blood analysis system of the disclosure, the sample is a whole blood sample, the first reagent includes a hemolytic agent for lysing red blood cells in the sample, and a latex reagent for performing immunoturbidimetric reaction with the analyte in the sample.

The blood analysis system further includes a second detection system, and the reaction portion further includes a second reaction chamber; the second detection system includes a light source, a flow chamber for cells to pass in line one by one, a liquid circuit system and a second detector;

the controller is further configured to: control the sampling portion to divide the sample into two parts, which are respectively transferred to the first reaction chamber and the second reaction chamber; control the reagent supply portion to transfer a second reagent to the second reaction chamber, wherein the sample reacts with the second reagent in the second reaction chamber to obtain a third test solution; control the second detection system, wherein the third test solution is transferred to the flow chamber under the driving of the liquid circuit system, the light source illuminates the flow chamber, and the second detector collects scattered light signals generated by the cells; and the processor is further configured to obtain the scattered light signals, and classify white blood cells in the sample into at least three types of lymphocytes, monocytes, and neutrophils according to the scattered light signals.

Further, in the blood analysis system, the second detection system further includes a third detector, and the third detector is configured to collect fluorescent signals generated by the cells, and the white blood cells are classified into at least four types of lymphocytes, monocytes, neutrophils, and eosinophils according to the scattered light signals and the fluorescent signals.

According to a specific embodiment, the second reagent includes a hemolytic agent and a staining agent.

According to a third aspect of the disclosure, a computer-readable medium for storing executable instructions is provided, wherein the computer-readable storage medium is configured to cause a processor to execute the executable instructions to implement the above-described method for detecting hook effect in turbidimetric inhibition immunoassay.

By utilizing the characteristic that the reaction degree of the initial reaction stage of the antigen-antibody is highly dependent on the reactant, the disclosure obtains reaction information of a certain stage of the reaction, especially the initial stage, and utilizes the reaction information in the initial stage of the reaction to determine whether there is hook effect for a sample, which greatly improves the alarm speed for abnormal samples with hook effect, thereby shortening the detection time of samples with hook effect. This has a positive effect on the improvement in the speed of outpatient test, especially the speed of blood protein test performed at the same time as routine blood test.

DETAILED DESCRIPTION

Figure 1:
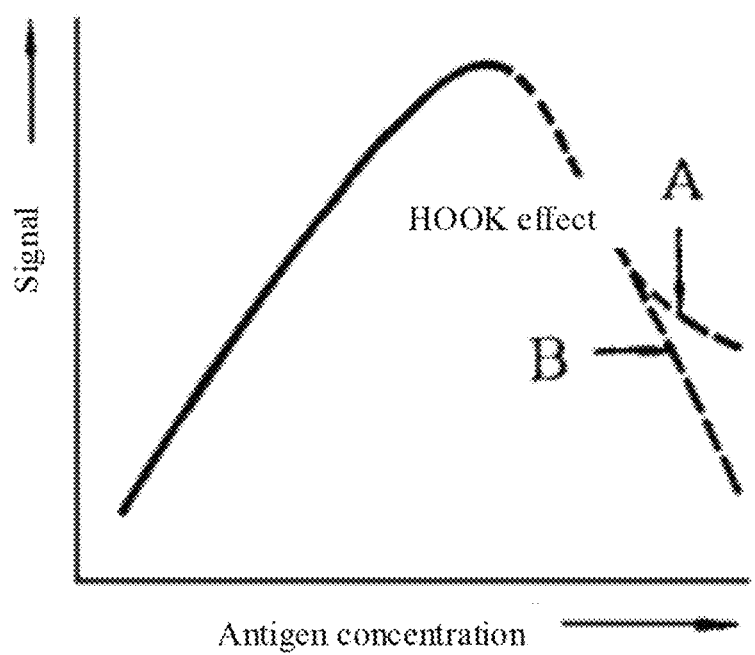
FIG. 1 is a schematic diagram showing hook effect by plotting amount of antibody-antigen precipitation against amount of antigen.

The technical solutions in the embodiments of the disclosure will be clearly and completely described below with reference to the specific embodiments of the disclosure and the accompanying drawings. The described embodiments are only some, but not all, embodiments of the disclosure. Based on the embodiments in the disclosure, all the other embodiments that would have been obtained by those of ordinary skill in the art without any inventive effort shall fall within the scope of protection of the disclosure.

Throughout the specification, unless otherwise specified, the terms used herein should be understood as the meanings commonly used in the art. Therefore, unless otherwise defined, all the technical and scientific terms used herein have the same meaning as commonly understood by those of skill in the art to which the disclosure belongs. In case of conflict, the definitions in this specification take precedence.

The term "turbidimetric inhibition immunoassay" is a method which detects concentration of an analyte based on particles suspended in the reaction system formed by immunoagglutination by measuring the change in intensity of transmitted light (i.e., transmission method), or by measuring the change in intensity of scattered light at a predetermined angle to the incident light (i.e., scattering method).

The methods for detecting hook effect of the disclosure are applicable to any turbidimetric inhibition immunoassay. A particularly preferred method is the latex-enhanced turbidimetric method.

In the latex-enhanced turbidimetric method, antibody corresponding to the analyte is coated on latex particles with a particle size of about 15-60 nanometers to increase the volume of the antigen-antibody conjugate, thereby enhancing the change in the intensity of transmitted light or scattered light to increase detection sensitivity. Commonly used latex particles are polymer particles such as polystyrene.

Specific types of turbidimetric inhibition immunoassay usually includes endpoint nephelometry and rate nephelometry, or an improved method that combines the two. The methods for detecting hook effect of the disclosure can be applied to any type of assay method without particular limitation.

It can be known from the methods of the disclosure which will be described in detail below that the methods of the disclosure are suitable for quickly determining whether a sample has hook effect in any turbidimetric inhibition immunoassay, and promptly terminating the testing of the sample with hook effect. For a sample without hook effect, the methods of the disclosure do not affect nor change the normal test procedure.

The methods for detecting hook effect of the disclosure utilizes light signals (such as light intensity or light absorbance) measured in a predetermined time period of the immune reaction of an analyte in a sample to generate a reaction curve, and utilizes distribution information of the reaction curve for the predetermined time period to determine whether the sample has hook effect. In the methods of the disclosure, only measurement information in a small predetermined time period within the entire reaction time are used to determine whether hook effect is present.

According to a first embodiment of the disclosure, after obtaining the reaction curve for the predetermined time period, a concentration of the analyte is estimated, and the estimated concentration of the analyte is used to obtain a reaction curve corresponding to this concentration in normal reaction state as a reference curve, and it is determined whether the sample has hook effect by comparing distribution information of the reaction curve of the analyte within the predetermined time period with that of the reference curve.

The "reference curve" in this context refers to a reaction curve of the analyte in a normal sample without hook effect at the estimated concentration, corresponding to the concentration of the analyte estimated from the measured values in the predetermined time period.

According to an embodiment, the time period is a predetermined time period $T_1$ to $T_n$ after the reaction starts. According to a specific embodiment, $T_1=0$, i.e., a time period from start of the reaction to a certain time point $T_n$. According to another specific embodiment, $T_1>0$, i.e., a time period from a certain time point $T_1$ to another time point $T_n$ after the reaction starts.

According to the disclosure, the predetermined time period is a time period in the first 90% of the reaction. That is, when the reaction progresses to 90% of the entire reaction time, the corresponding time point is $T_{90}$, then $T_n \leq T_{90}$. For example, the predetermined time period may be a time period in the first 80%, the first 70%, the first 50%, the first 30%, or even the first 10% of the entire reaction.

When in the curve of the reaction signal data of the immune reaction or the data set obtained by performing derivation on the reaction signal data against the reaction time, a maximum value appears in the middle of the curve (that is, when the trend of the slope of the reaction curve changes), for example, when the reaction rate reference curve has a maximum value in the middle, the predetermined time period is a time period before the entire reaction reaches the maximum value. Which part of the entire reaction process is selected as the predetermined time period varies according to the analyte. It is usually determined empirically based on the specific circumstances of the assay. According to the disclosure, the predetermined time period is preferably a time period after the reaction starts, i.e., $T_1=0$. According to this preferred manner, it is helpful to identify samples with hook effect as soon as possible, and stop testing.

Typically, the predetermined time period for generating the reaction curve of the analyte accounts for 10% to 70% of the entire reaction time, such as a time period accounting for 15%, 20%, 25%, 30%, 35%, 40%, 45%, 50% or 60% of the entire reaction time. According to a preferred embodiment, the time period for generating the reaction curve of the analyte accounts for 15%-50% more preferably 15%-40% of the entire reaction time.

According to the most preferred embodiment, the time period for generating the reaction curve of the analyte is the reaction curve in the earlier section after the reaction starts (i.e., $T_1=0$), the endpoint $T_n$ may be a time period during which the reaction has progressed 10% to 70% (i.e., $T_n=T_{10\text{-}70}$), preferably 10% to 50% (i.e., $T_n=T_{10\text{-}50}$), more preferably 10% to 40% (i.e., $T_n=T_{10\text{-}40}$).

According to the methods of the disclosure, in the above time period, the actual reaction curve is obtained according to the actually detected information, such as absorbance, and the estimated concentration of the analyte is obtained according to a stored standard curve. The method for estimating the analyte concentration is the same as the conventional method for obtaining the analyte concentration, except that in the methods of the disclosure, the concentration of the analyte is estimated using only the detection information of the reaction over a time period, especially the reaction initiation period.

Further, the methods of the disclosure utilize the estimated concentration of the analyte to obtain a corresponding reference curve. As mentioned above, by comparing the distribution information of the actual reaction curve and the reference reaction curve, it is possible to quickly determine whether the sample has hook effect.

According to the methods of the disclosure, hook effect is determined by means of the reaction curve obtained in a relatively short predetermined time period, so whether hook effect is present can be determined in a relatively short time period after start of the reaction, and the testing can be terminated as soon as possible in the presence of hook effect.

In the event that hook effect is detected in a sample, the testing is terminated and the reaction chamber is washed or another reaction chamber is used for re-preparing or aspirating the sample which is retested after appropriate dilution.

In the absence of hook effect in a sample, the reaction continues to completion and test results are reported.

The methods of the disclosure are particularly advantageous for obtaining test results as early as possible in whole blood test. Among the outpatient clinical blood tests in hospitals, routine blood test is the most common test item. The conventional automatic blood analyzers can quickly complete various test items such as red blood cell count, white blood cell count and platelet count and white blood cell classification in routine blood test. The detection of specific proteins in blood is relatively slow. Most commonly, such as CRP testing time often determines the speed of outpatient testing.

In the conventional method, if a sample has hook effect (in patients, this situation often exists), it needs to be determined at the end of the first test, and then the sample would be retreated and tested again. This further affects the speed of outpatient testing. The methods of the disclosure thus help to speed up outpatient testing. For example, if the CRP measurement time is 60 s, the methods of the disclosure can complete the recognition within 10-20 s.

The detection device used for turbidimetric inhibition immunoassay may be a turbidimeter or a nephelometer, specifically, a scattered light detector or a transmitted light detector. Measurements can be made in the ultraviolet or near-ultraviolet to visible range (typically 300-800 nm). The temperature of the reaction system during measurement is usually ambient temperature, for example, 20° C. to 40° C., preferably about 37° C.

The term "sample" or "sample to be tested" in this context generally refers to a blood sample, in particular a whole blood sample. Here, the sample to be tested is usually a peripheral blood or venous blood sample derived from mammal, especially a blood sample derived from human. The sample has undergone the necessary treatment before the immune reaction. The treatment includes, but is not limited to, such as anticoagulation treatment, dilution treatment, hemolytic treatment, and the like.

When performing turbidimetric inhibition immunoassay, the sample is first pipetted into a reaction chamber from a sample tube, and reaction reagents are added sequentially or simultaneously to start reaction and testing is started at the same time. The reaction reagents are reagents commonly used in the art and that can make immunoreaction with the analyte, such as latex coated with antibody or antigen, and reagents that aggregate immune complexes, such as polyethylene glycol. This is not repeated herein. The reaction reagents may be one solution or various solutions, such as a hemolytic agent for lysing red blood cells in a whole blood sample, a polyethylene microsphere latex reagent coated with antibody, a buffer for diluting a whole blood sample, and the like.

The term "analyte" herein refers to antigen, antibody, protein, polypeptide, etc. in a sample, especially a blood sample. Specifically, it may be, but not limited to, for example, C-reactive protein (CRP), serum amyloid A protein (SAA), procalcitonin (PCT for short), interleukin-6 (IL-6 for short), human chorionic gonadotropin, growth hormone, luteinizing hormone, alpha-fetoprotein, carcinoembryonic antigen, etc.

Figure 2:
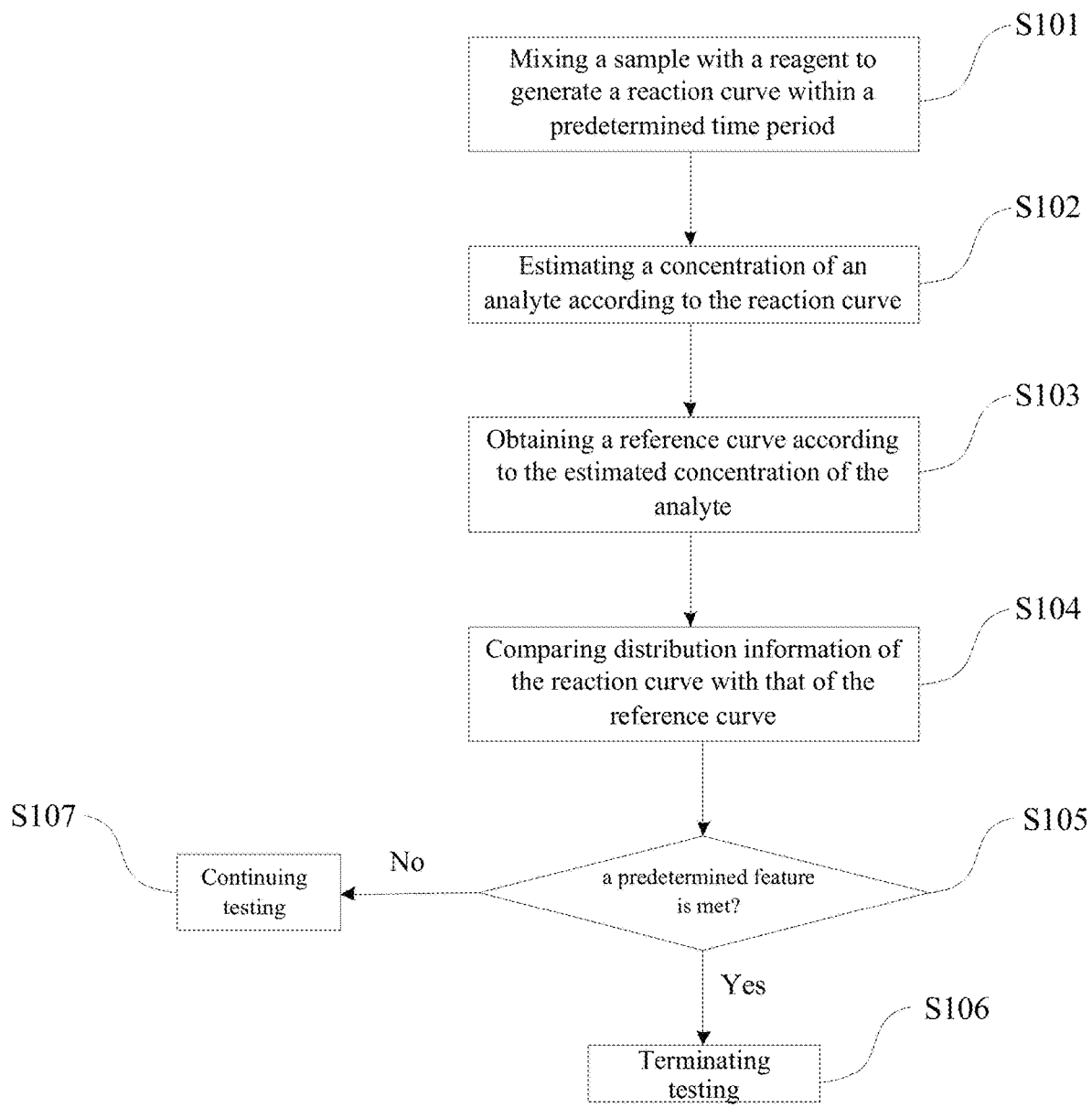
FIG. 2 is a flowchart according to a first embodiment of the disclosure.

The first embodiment of the disclosure will be described in further detail below with reference to FIG. 2. The method of the disclosure includes the following steps. In step S101, firstly, a sample is mixed with a reaction reagent so that an analyte in the sample starts to react; then, a measured value $A_i$ at a time point $T_i$ in a predetermined time period $T_1$ to $T_n$ after the reaction starts is obtained, where i is an integer from 1 to n, so that a plurality of measured values $A_1$ to $A_n$ are obtained to generate a reaction curve for said time period. Next, in step S102, a concentration $C_e$ of the analyte is estimated based on the reaction curve for said time period and a pre-stored calibration curve. In step S103, a pre-stored reference curve corresponding to the concentration is obtained according to the estimated concentration $C_e$ of the analyte. Finally, in step S104, distribution information of the reaction curve for the time period is compared with distribution information of the reference curve for the corresponding time period. In step S105, determination is made, that is, if a predetermined feature is met (such as difference between the distribution information of the reaction curve and the reference curve is higher than a predetermined threshold or change trend of the distribution information of the two conforms to a certain rule), then it is determined that there is hook effect, and step S106 is performed to terminate the testing; if not, step S107 is performed to continue the testing.

Specifically, degree of reactivity $R_d$ is calculated based on the reaction curve for the predetermined time period, and the concentration $C_e$ of the analyte is estimated through the calibration curve according to the degree of reactivity $R_d$, where the degree of reactivity $R_d$ is the difference $(A_n-A_1)$ between the measured value $(A_n)$ at the end of the time period $(T_n)$ and the measured value $(A_1)$ at the beginning of the time period $(T_1)$: $R_d=A_n-A_1$.

The applicant found through research that, for a sample without hook effect, the degree of reactivity within a time period of reaction is consistent with the calibration curve, so the estimated concentration of the analyte is close to the concentration measured after the entire reaction is completed. The reference curve under normal reaction state (without HOOK effect) obtained according to the estimated concentration is consistent with or approach the reaction curve of the sample at the beginning of the reaction.

Figure 3:
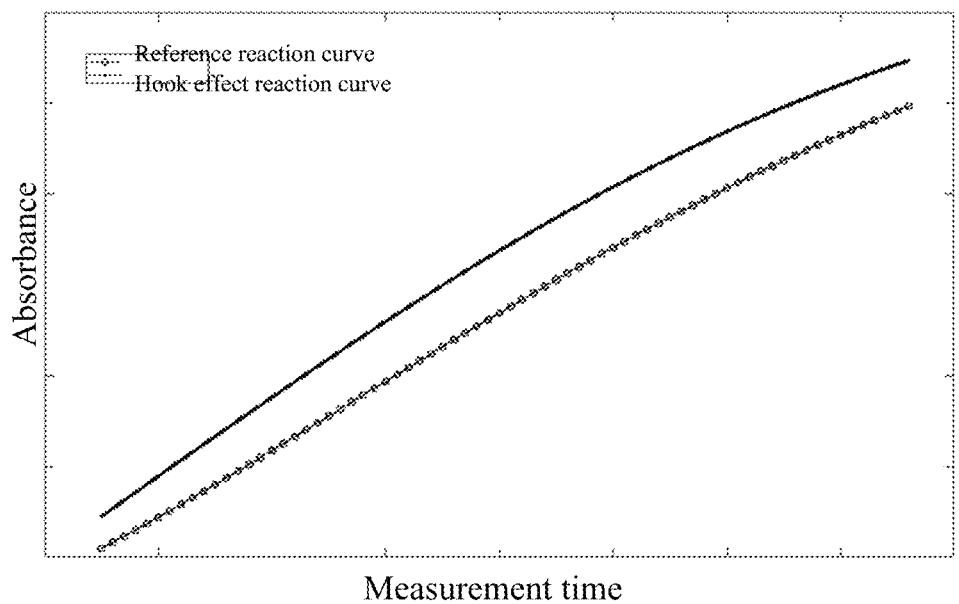
FIG. 3 is a comparison diagram of a reaction curve with hook effect and a reference curve according to an embodiment of the disclosure.

Conversely, for a sample with hook effect, the concentration of the analyte in the sample exceeds the linear portion of the calibration curve. Therefore, at the beginning of the reaction, the concentration of the analyte estimated from the reaction curve would be significantly higher, and the reference curve obtained therefrom would deviate from the reaction curve of the sample with hook effect (see FIG. 3, which shows the comparison chart of the change of absorbance over reaction time between the reaction curve of the sample with hook effect and the reference curve in a time period at the beginning of the reaction).

Figure 4:
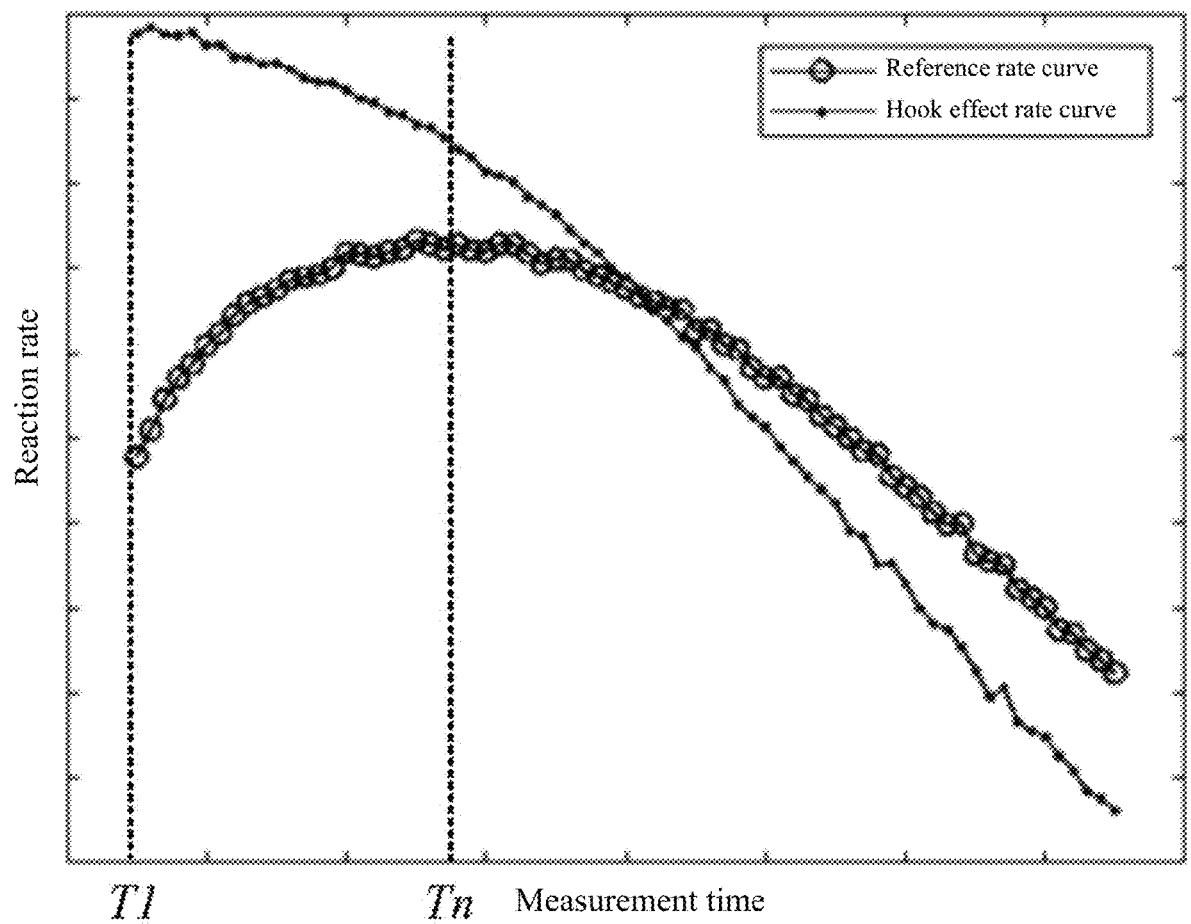
FIG. 4 is a comparison diagram of curves of reaction rate as a function of time obtained by performing first derivation on the reaction curve and the reference curve in FIG. 3 with respect to time respectively according to an embodiment of the disclosure.
Figure 5:
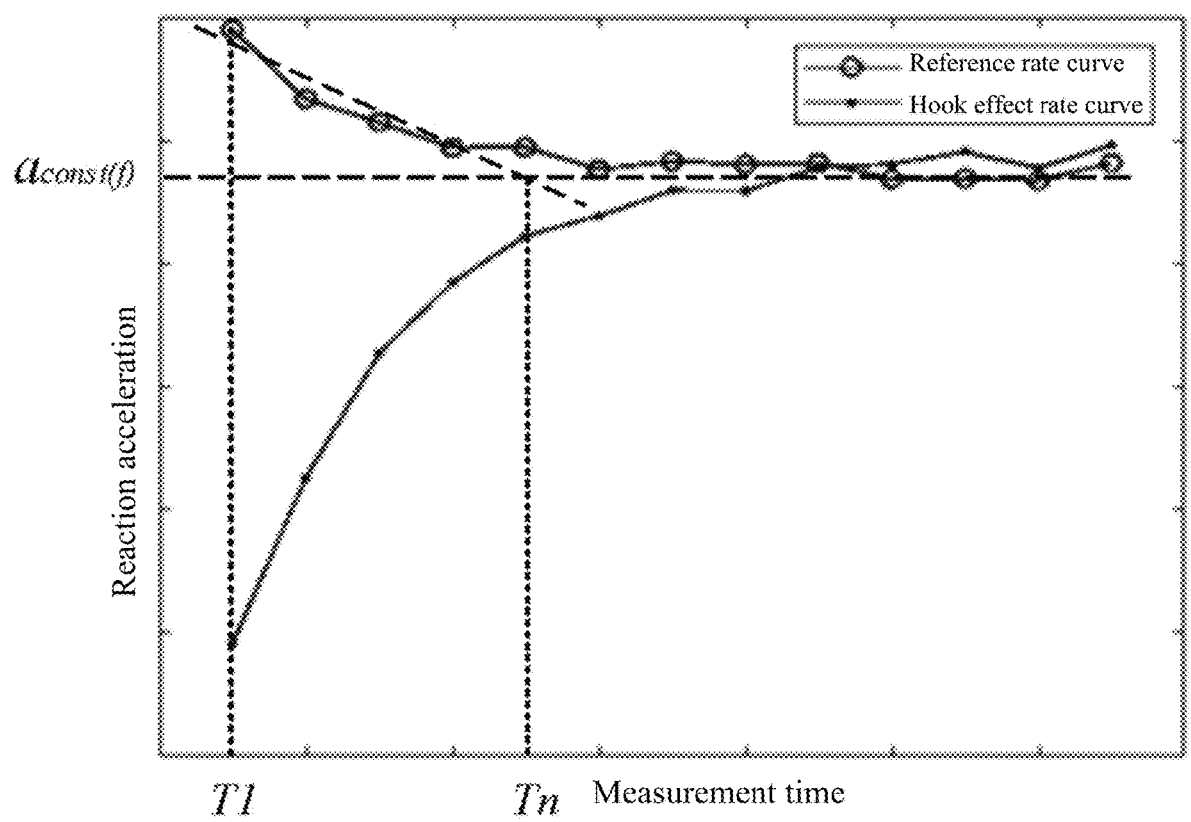
FIG. 5 is a comparison diagram of curves of reaction acceleration as a function of time obtained by performing second derivation on the reaction curve and the reference curve in FIG. 3 with respect to time respectively according to an embodiment of the disclosure.

Likewise, reaction rate and reaction acceleration of the sample with hook effect would be significantly different from speed and acceleration of the conventional reaction represented by the reference curve (see FIGS. 4 and 5).

According to a specific solution of this embodiment, when the difference between the distribution information of the reaction curve and the distribution information of the reference curve within the time period of $T_1$ to $T_n$ is lower than a predetermined threshold, it is determined as having no hook effect; and when the difference between the distribution information of the reaction curve and the distribution information of the reference curve within the time period of $T_1$ to $T_n$ is higher than a predetermined threshold, it is determined as having hook effect.

In the disclosure, the reaction time and reaction distribution information under measurement conditions are applied to the methods for detecting hook effect. The reaction distribution information includes a measured value (for example, absorbance) feature, a reaction rate feature, and/or a reaction acceleration feature.

The measured value feature may directly include an optical measured value (for example, an absorbance value) within the predetermined time period, or an average measured value within the predetermined time period, or both.

According to a specific embodiment, in the determination step, an optical measured value $A_i$ of the reaction curve at a certain time point $T_i$ and a reference value $A_{i(f)}$ of the reference curve at a corresponding time point are substituted into the following formula to obtain a reaction difference $\delta_i$ %:

$$\delta_i \% = [(A_i - A_{i(f)})/A_{i(f)}] \times 100\%.$$

When the reaction difference $\delta_i$ % is greater than or equal to a predetermined threshold $\delta 1$, it is determined that the sample has hook effect.

According to another specific embodiment, an average measured value $\overline{A}$ of the reaction curve within the time period $T_1$ to $T_n$ and an average reference value $\overline{A}_{(f)}$ of the reference curve within the corresponding time period are substituted into the following formula to obtain an average reaction difference Δ% for the time period:

$$\Delta \% = [(\overline{A} - \overline{A}_{(f)})/\overline{A}_{(f)}] 100\%.$$

When the average reaction difference Δ % is greater than or equal to a predetermined threshold Δ1, it is determined that the sample has hook effect.

According to yet another embodiment, the reaction difference $\delta_i$ % and the average reaction difference Δ % are calculated according to the above embodiments. When the reaction difference $\delta_i$ % is greater than or equal to a predetermined threshold δ2, and the average reaction difference Δ % is greater than or equal to a predetermined threshold Δ2, it is determined that the sample has hook effect.

The distribution information may also include a value of a reaction rate or a reaction acceleration within the predetermined time period, or an average reaction rate or an average reaction acceleration value within the predetermined time period.

Specifically, first derivation is performed on the reaction curve A=f(T) and the reference curve $A_{(f)}$=f($T_{(f)}$) respectively with respect to time to obtain curves of reaction rate as a function of time v=A'=f'(T) and v'=$A_{(f)}$'=f'($T_{(f)}$).

An reaction rate value $v_i$ at the time $T_i$ and a reference reaction rate value $v_{i(f)}$ are substituted into the following formula to obtain a reaction rate difference $\delta v_i$ %:

$$\delta v_i \% = (|v_i - v_{i(f)}|) \times 100\%.$$

When $\delta v_i$ % is greater than or equal to a predetermined threshold δv1, it is determined that the sample has hook effect.

Alternatively, an average reaction rate value $\bar{v}$ within the time period $T_1$ to $T_n$ and an average reference reaction rate value $\bar{v}_{(f)}$ within the corresponding time period are substituted into the following formula to obtain an average reaction rate difference Δv % for the time period:

$$\Delta v \% = (|\bar{v} - \bar{v}_{(f)}|/\bar{v}_{(f)}) \times 100\%$$

When Δv % is greater than or equal to a predetermined threshold Δv1, it is determined that the sample has hook effect.

According to yet another embodiment, the reaction difference $\delta v_i$ % and the average reaction difference Δv % are calculated according to the above embodiment. When the reaction difference $\delta v_i$ % is greater than or equal to a predetermined threshold δv2, and the average reaction difference Δv % is greater than or equal to a predetermined threshold Δv2, it is determined that the sample has hook effect.

In the reaction rate reference curve, the rate of reaction of the analyte with the detection reagent increases first and then decreases, and the curve has a maximum point. That is, during the test process, a maximum reaction rate occurs in the middle of the reaction (see FIG. 4).

However, in a sample with hook effect, the rate of reaction of the analyte with the detection reagent generally continues to decrease, the actual reaction rate is much higher than the reference reaction rate in the early stage of the reaction, but is often lower than the reference reaction rate in the later stage.

According to a specific example, the certain time point $T_i$ or the certain time period $T_1$ to $T_n$ selected for the comparison of the difference is preferably selected before the time point (i.e., $T_{max}$) corresponding to the maximum reference reaction rate appearing in the reference reaction rate curve.

In addition, it is found by research that in a sample with hook effect, the reaction rate curve intersects with the reference reaction rate curve. In this case, the certain time point $T_i$ selected for the comparison of the difference should be avoided to be selected near the time point corresponding to the intersection (i.e., actual reaction rate=reference reaction rate), and is preferably selected before the corresponding time point. When selecting the certain time period $T_1$ to $T_n$, the time period from start of the reaction to the time point corresponding to the intersection may also be selected.

Different samples have reaction curves and reference curves of different shapes. Those skilled in the art can understand that samples that are known to have no hook effect and that have hook effect can be counted, and appropriate value of $T_i$ or $T_n$ can be obtained according to the above principles.

The reaction acceleration may be obtained by second derivation. Specifically, a second derivation is performed on the reaction curve A=f(T) and the reference curve $A_{(f)}$=f($T_{(f)}$) respectively to obtain curves of reaction acceleration as a function of time a=A''=f''(T) and $a_{(f)}$=$A_{(f)}$''=f''($T_{(f)}$).

a reaction acceleration value $a_i$ at a time point $T_i$ and a reference reaction acceleration value $a_{i(f)}$ at a corresponding time point are substituted into the following formula to obtain a reaction acceleration difference $\delta a_i$ %:

$$\delta a_i \% = |(a_i - a_{i(f)})/a_{i(f)}| \times 100\%$$

When $\delta a_i$% is greater than a predetermined threshold δa1, it is determined that the sample has hook effect.

Alternatively, an average reaction acceleration value $\bar{a}_i$ within the time period $T_1$ to $T_n$ and an average reference reaction acceleration value $\bar{a}_{(f)}$ within the corresponding time period are substituted into the following formula to obtain an average reaction acceleration difference Δa % for the time period:

$$\Delta a \% = |(\bar{a} - \bar{a}_{(f)})/\bar{a}_{(f)}| \times 100\%$$

When Δa % is greater than a predetermined threshold Δa1, it is determined that the sample has hook effect.

According to yet another embodiment, the reaction difference $\delta a_i$ % and the average reaction difference Δa % are calculated according to the above embodiment. When the reaction difference $\delta a_i$ % is greater than or equal to a predetermined threshold δa2, and the average reaction difference Δa % is greater than or equal to a predetermined threshold Δa2, it is determined that the sample has hook effect. In this example, the predetermined time period is preferably selected to be a time period before the reaction acceleration of the reference curve enters a plateau $a_{const(f)}$ (if any) (see FIG. 5).

The above predetermined thresholds may be the same or different. The above predetermined thresholds vary according to the testing equipment used, testing methods, samples and analytes, etc. The above predetermined thresholds are usually a statistical or empirical value and is a function of $T_n$.

According to yet another embodiment, the distribution information may also include a contour line of change of the reaction rate or reaction acceleration over time within the predetermined time period, and whether the sample has hook effect is determined according to the change trend of the contour line.

Specifically, referring to FIG. 4, in the time period of $T_1$ to $T_n$, the reaction rate curve has an overall trend that the reaction rate decreases over time, at the same time, the reference reaction rate curve has an overall trend that the reference reaction rate first increases and then decreases over time. If the above-mentioned feature contour exists, it can be determined that the sample has hook effect.

In other words, it is determined that the sample has hook effect when the reaction rate values on the smoothed reaction rate curve at two different times $T_i$ and $T_j$ within the time period $T_1$ to $T_n$ satisfy $v_i > v_j$ (where j is an integer from 2 to n, and j>i) and there is a maximum value $v_{max(f)}$ on the fitted reference reaction rate curve within the corresponding time period.

Alternatively, referring to FIG. 5, it is determined that the sample has hook effect when within the time period $T_1$ to $T_n$, most of the reaction acceleration values at two adjacent times $T_i$ and $T_j$ satisfy $a_i < a_j$, and within the corresponding time period $T_{f1}$ to $T_{fn}$, most of the reference reaction acceleration values at two adjacent times $T_{fi}$ and $T_{fj}$ satisfy $a_{fi} > a_{fj}$, where j is an integer from 2 to n, and j>i.

According to a second embodiment of the disclosure, after obtaining the reaction curve of the analyte in the tested sample in the predetermined time period from start of the reaction, a contour line of the change of the reaction rate or reaction acceleration over time within the predetermined time period is further obtained from the reaction curve, and it is determined whether the sample has hook effect according to the change trend of the contour line. In this embodiment, there is no need to estimate the concentration of the analyte to obtain a reference curve.

In this embodiment, the definitions of the sample, the analyte and the predetermined time period are as described above. A reaction curve for the predetermined time period is obtained in the same way.

Figure 6:
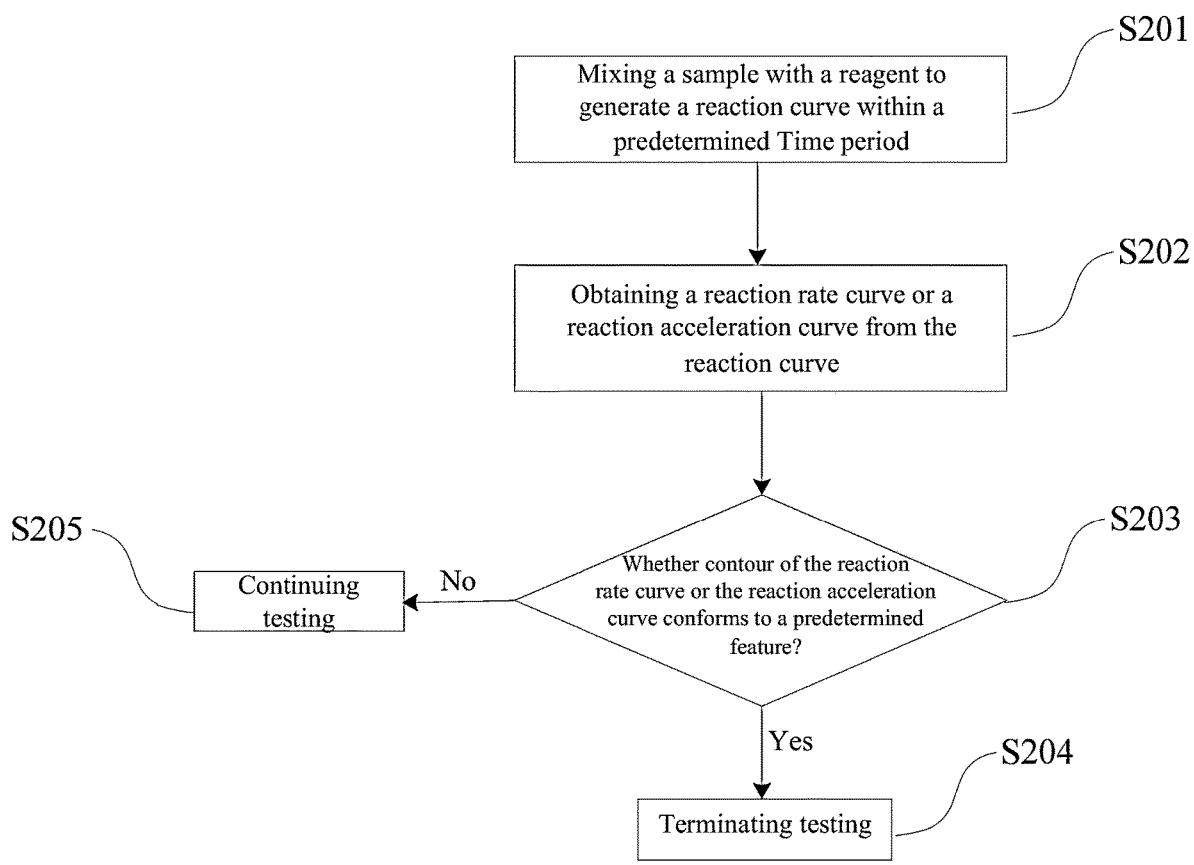
FIG. 6 is a flowchart according to a second embodiment of the disclosure.

Referring to FIG. 6, the second embodiment will be described in detail. According to this embodiment, in step S201, after a sample is mixed with a reaction reagent so that an analyte in the sample starts to react, a measured value $A_i$ at a time point $T_i$ within the time period $T_1$ to $T_n$ after the reaction starts is obtained, where i is an integer from 1 to n, so that a plurality of measured values $A_1$ to $A_n$ are obtained to generate a reaction curve for said time period. In step S202, a derivation is performed on the reaction curve $A = f(T)$ for the time period with respect to time T, wherein a reaction rate curve is obtained by performing first derivation, and a reaction acceleration curve is obtained by performing second derivation. Then, determination step S203 is performed, and it is determined whether the sample has hook effect based on a contour of the curve after the derivation. When there is hook effect, step S204 is performed to terminate the testing; otherwise, step S205 is performed to continue the current testing.

Specifically, first derivation is performed on the reaction curve $A = f(T)$ with respect to time T to obtain a curve of reaction rate as a function of time $v = A' = f'(T)$. It is determined that the sample has hook effect when most of the reaction rate values at two adjacent different times $T_i$ and $T_j$ within the time period $T_1$ to $T_n$ satisfy $v_i > v_j$, where j is an integer from 2 to n, and j>i.

According to another specific embodiment, second derivation is performed on the reaction curve $A = f(T)$ with respect to time T to obtain a curve of reaction acceleration as a function of time $a = A'' = f''(T)$. It is determined that the sample has hook effect when most of the reaction acceleration values at two adjacent different times $T_i$ and $T_j$ within the time period $T_1$ to $T_n$ satisfy $a_i < a_j$, where j is an integer from 2 to n, and i<j.

When it is determined that the sample has hook effect, the testing is terminated; otherwise the testing is continued.

Optionally, the sample is re-prepared or re-aspirated into the reaction chamber and re-tested after proper dilution at an increased dilution ratio.

The disclosure also relates to a blood analysis system capable of implementing the above determination methods.

The blood analysis system includes a sampling portion, a reagent supply portion, a reaction portion including a reaction chamber, a data processing module and a controller.

Figure 7:
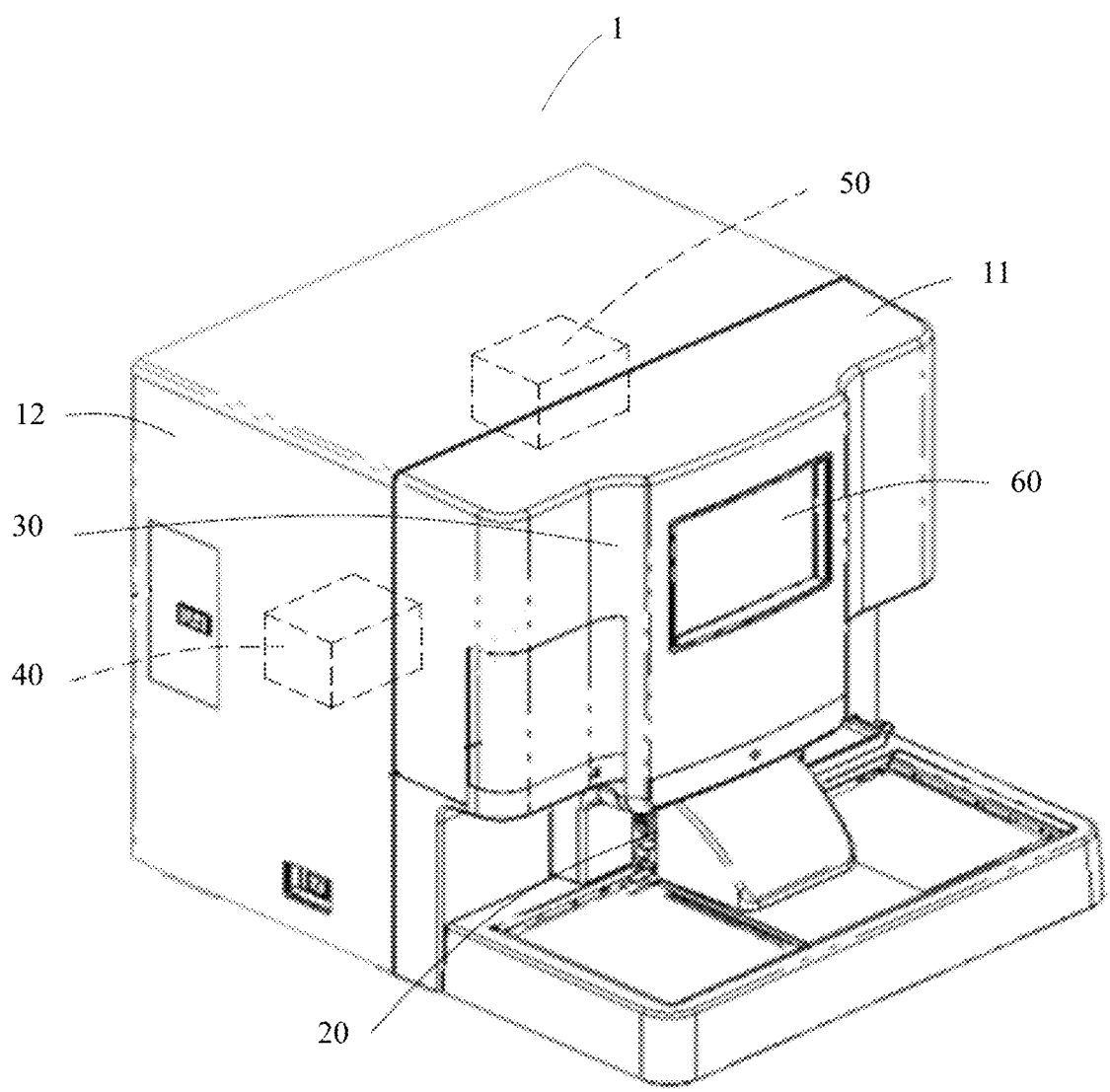
FIG. 7 is a schematic diagram of a blood analysis system according to an embodiment.

Referring to FIG. 7, a specific blood analysis system, namely a fully automatic blood analyzer 1, is schematically shown. The blood analyzer 1 has a first housing 11, a second housing 12, a sampling portion 20, a reaction portion 30, a reagent supply portion (not shown), a detection system 40, a host system 50 and an output portion 60. In practical applications, the output portion 60 may be a user interface. In this embodiment, the detection system 40 and the host system 50 are arranged inside the second housing 12. The reaction portion 30 is arranged inside the first housing 11. The detection system is close to a reaction chamber (not shown) of the reaction portion 30 to facilitate detection. The output portion 60 and the sampling portion 20 are arranged on the outer surface of the first housing 11.

The sampling portion 20 has a sampling needle used to collect a blood sample, and transfers the collected blood sample to the reaction chamber of the reaction portion 30.

The reagent supply portion is configured to store the above-mentioned first reaction reagent for reacting with the blood sample and other necessary reagents and supplies corresponding reagents to the reaction portion as needed.

The reaction portion 30 may include a first reaction chamber, and the first reaction chamber is configured so that the blood sample from the sampling portion and the first reaction reagent from the reagent supply portion react in the reaction chamber to generate antibody-antigen complex particles.

The detection system 40 includes a light source and a detector for detecting the reaction system in the reaction chamber and is configured to obtain measured values of the reaction system. The detector may include a nephelometer and/or a turbidimeter.

The host system 50 includes a processor, a storage, and a controller. The controller is coupled to the sampling portion, the reagent supply portion, the reaction portion and the detection system, and is configured to control actions of the sampling portion, the reagent supply portion, the reaction portion and the detection system. The processor is coupled to the detection system 50. The storage may be a transitory computer-readable storage medium in which a computer program is stored. When the computer program is executed by the processor, the above-mentioned method for detecting hook effect of the disclosure is executed. The controller is also operably connected to the processor for receiving test results from the processor.

In the disclosure, when the processor obtains the result that the sample has hook effect, the controller controls the detection system to stop testing.

Further, the system of the disclosure can also automatically perform retesting. The controller further issues an instruction for retesting. Under the control of the controller, the liquid in the reaction chamber is removed and the reaction chamber is washed; The sampling portion 20, the reaction portion 30, the reagent supply portion, and the detection system 40 cooperate with each other again to perform retesting. The sampling portion is controlled to sample the sample again, and transfer the blood sample to the first reaction chamber of the reaction portion; the reagent supply portion is controlled to supply the first reaction reagent to the first reaction chamber to prepare a second test solution, where a dilution factor of the sample in the second test solution is greater than a dilution factor of the sample in the first test solution; and the detection system is controlled to test the second test solution again.

The output portion 60 is configured to output the test results of the analyte in the sample according to the instruction issued by the controller when the processor obtains a result that the corresponding sample does not have hook effect.

The blood analysis system of the disclosure may further have an alarm apparatus (not shown) for alarming when the data processing module determines that the sample has hook effect.

According to a further embodiment, the blood analysis system of the disclosure further includes a second detection system, and the reaction portion further includes a second reaction chamber.

The second detection system includes a light source, a flow chamber for the cells to pass in line one by one, a liquid circuit system and a second detector.

According to this embodiment, the blood analysis system of the disclosure can simultaneously perform routine blood test and turbidimetric inhibition immunoassay of a specific protein (for example, C-reactive protein) on a whole blood sample.

In this embodiment, the controller controls the sampling portion to divide the sample into two parts, which are respectively transferred to the first reaction chamber and the second reaction chamber.

The test using turbidimetric inhibition immunoassay is as described above. In another test, such as routine blood test, the controller controls the reagent supply portion to transfer the second reagent to the second reaction chamber. The sample reacts with the second reagent in the second reaction chamber to obtain a third test solution.

An example of the second reagent may include, but is not limited to, a hemolyzing agent and a staining agent.

The second detection system is controlled, and under the driving of the liquid circuit system, the third test solution is transferred to the flow chamber, the light source illuminates the flow chamber, and the second detector collects scattered light signals generated by the cells.

The processor obtains the scattered light signals, and classifies white blood cells in the sample into at least three types of lymphocytes, monocytes and neutrophils according to the scattered light signals.

The second detection system further includes a third detector, and the third detector collects fluorescent signals generated by the cells, and the white blood cells are classified into at least four types of lymphocytes, monocytes, neutrophils and eosinophils according to the scattered light signals and the fluorescent signals.

According to the scattered light and fluorescence signals collected by the second detection system, red blood cells, white blood cells, platelets, etc. can be further counted and classified.

The disclosure further provides a computer-readable storage medium. The computer-readable storage medium stores executable instructions, and when the executable instructions are executed by the above-mentioned processor, the steps of the aforementioned method for detecting hook effect in turbidimetric inhibition immunoassay are implemented. The computer-readable storage medium may be the aforementioned storage or a component thereof, in which the computer program is stored and the computer program is executed by the processor of the blood analysis system to perform the steps of the aforementioned method.

The computer-readable storage medium may be FRAM, ROM, PROM, EPROM, EEPROM, Flash Memory, magnetic surface memory, optical disk or CD-ROM, etc., and may also be various devices including one or any combination of the foregoing storage media.

The advantages of the disclosure are further illustrated by the specific examples below.

EXAMPLE 1

Figure 8:
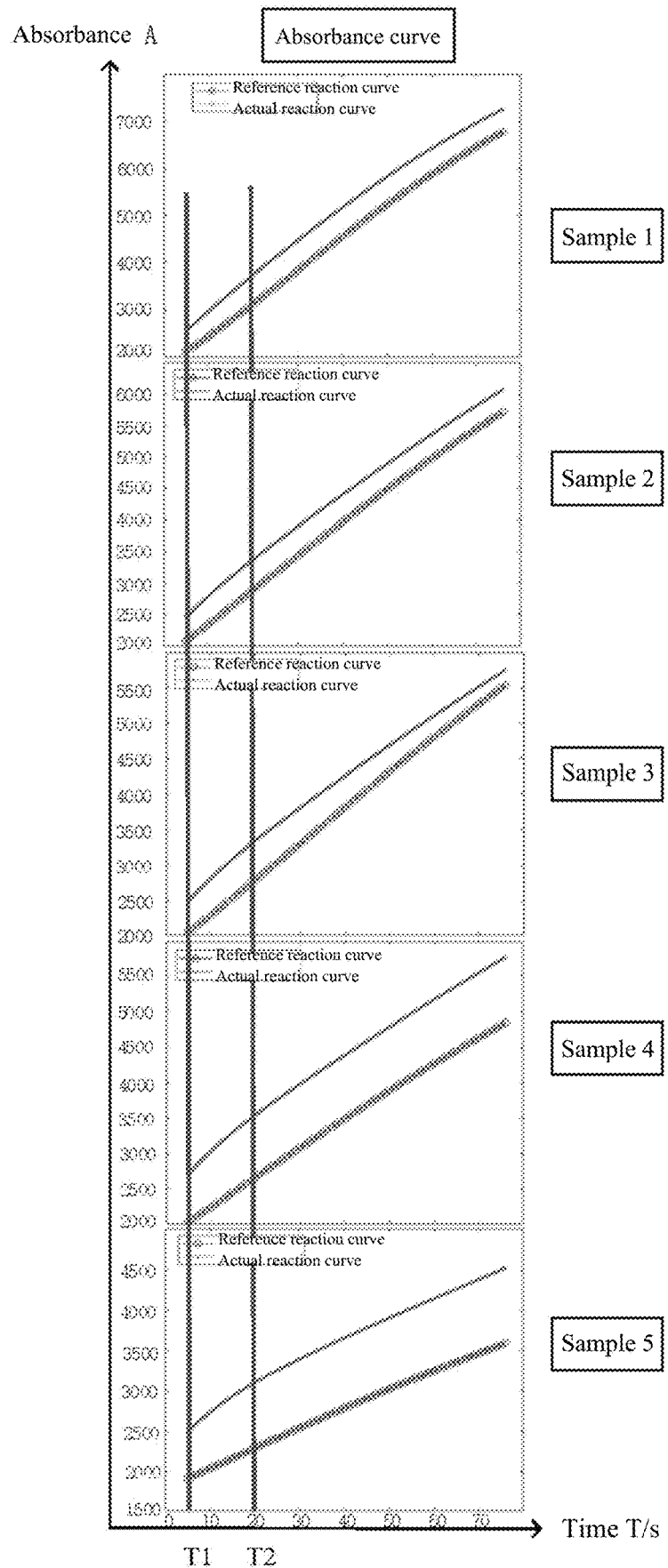
FIG. 8 is a graph showing actual reaction curves obtained by testing 5 samples of Example 1 and corresponding reference reaction curves.

In serum amyloid A (SAA) detection, 5 whole blood samples known to have hook effect were tested on Mindray BC-5390CRP. The longest test time for each sample is 80 s. Signal per second was acquired to plot an original reaction curve (i.e., absorbance curve, see FIG. 8) for each of these samples.

The signal values $A_1$ and $A_2$ at the time point $T_1=5$ s and $T_2=20$ s on the original reaction curve were obtained for each of these samples. The signal value (i.e. absorbance) per second from the time point $T_1=5$ s to $T_2=20$ s was used to calculate a signal mean $\overline{A}$. An SAA concentration value $C_e$ for each of these samples was estimated according to the original reaction curve between $T_1$ to $T_2$ (see Table 1 below). Then, according to the estimated concentration $C_e$, a curve corresponding to the concentration $C_e$ was acquired from stored reference curves, and the curve was used as the reference reaction curve (see FIG. 8).

Similarly, corresponding signal values $A_{1(f)}$ and $A_{2(f)}$ at the time $T_1$ and $T_2$ on the reference reaction curve were obtained. A signal mean $\overline{A}_{(f)}$ was calculated from the signal value per second between $T_1$ to $T_2$ (see Table 2 below).

TABLE 1

Original measurement results and estimated concentrations of SAA in the samples

| | Estimated concentration $C_e$ (mg/L) | $T_1$ signal value $A_{i1}$ | $T_2$ signal value $A_{i2}$ | $T_1$ to $T_2$ mean $\overline{A}$ |
|---|---|---|---|---|
| Sample 1 | 309.48 | 2542.54 | 3733.39 | 3151.22 |
| Sample 2 | 205.22 | 2454.43 | 3372.47 | 2934.58 |
| Sample 3 | 177.95 | 2493.95 | 3345.99 | 2943.17 |
| Sample 4 | 161.76 | 2705.94 | 3543.66 | 3154.74 |
| Sample 5 | 109.74 | 2479.06 | 3096.18 | 2817.67 |

TABLE 2

Corresponding signal values and signal mean according to the reference reaction curves $T_1 = 5$ s and $T_2 = 20$ s

| Reference curve | $T_1$ signal value $A_{1(f)}$ | $T_2$ signal value $A_{2(f)}$ | $T_1$ to $T_2$ mean $\overline{A}_{(f)}$ |
|---|---|---|---|
| Sample 1 | 2111.96 | 3121.05 | 2604.53 |
| Sample 2 | 2085.77 | 2889.90 | 2482.04 |
| Sample 3 | 2055.72 | 2792.18 | 2416.82 |
| Sample 4 | 2031.55 | 2660.25 | 2342.76 |
| Sample 5 | 1911.78 | 2285.30 | 2095.58 |

The difference between the signal value of the original reaction curve and the signal value of the reference reaction curve at each of $T_1$ and $T_2$ time points was calculated according to the following formula $$\delta_i \% = [(A_i - A_{i(f)})/A_{i(f)}] \times 100\%$$

$T_i = 5$ s or 20 s, when $\delta_i \% \geq 15\%$, the presence of hook effect is determined.

In this example, $\delta_i \%$ at both 5th second and 20th second is greater than 15%. In some occasions where the precision of the alarm is not high, the alarm of whether the sample has hook effect can be carried out according to whether $\delta_i \%$ at 5th second or 20th second is greater than a threshold. It is also possible to alarm according to whether $\delta_i$ % at other time points between $T_1$ and $T_2$, for example at 10th second or 15th second is greater than a threshold.

Alternatively, the difference between the signal mean of the original reaction curve and the signal mean of the reference reaction curve within 5th second-20th second was calculated according to the following formula:

$$\Delta\% = [(\overline{A} - \overline{A}_{(f)})/\overline{A}_{(f)}] \times 100\%$$

When $\Delta\% \geq 15\%$, the presence of hook effect is determined.

Specific results are as shown in Table 3.

TABLE 3 signal value difference at $T_1 = 5$ s and $T_{16} = 20$ s and signal mean difference within 5-20 s

| | Signal value difference at $T_1$ $\delta_1$ % | Signal value difference at $T_2$ $\delta_2$ % | Signal mean difference $\Delta$ % in $T_1$ to $T_2$ |
|---|---|---|---|
| Sample 1 | 20.39% | 19.62% | 20.99% |
| Sample 2 | 17.68% | 16.70% | 18.23% |
| Sample 3 | 21.32% | 19.83% | 21.78% |
| Sample 4 | 33.20% | 33.21% | 34.66% |
| Sample 5 | 29.67% | 35.48% | 34.46% |

As can be seen from Table 3 above, the corresponding reference curve is acquired from the stored calibration curves according to the estimated SAA concentration within the first 15 s of the reaction, the original signal value at a certain time point in the first 15 s of the reaction and the signal value at the corresponding time point of the reference curve are compared with each other, and when the difference is greater than 15%, it is determined that the sample has hook effect.

Alternatively, the average value of the original signal within the first 15 s of the reaction is compared with the average value of the reference curve within the corresponding time period, and when the difference is greater than 15%, it is determined that the sample has hook effect.

EXAMPLE 2

Figure 9:
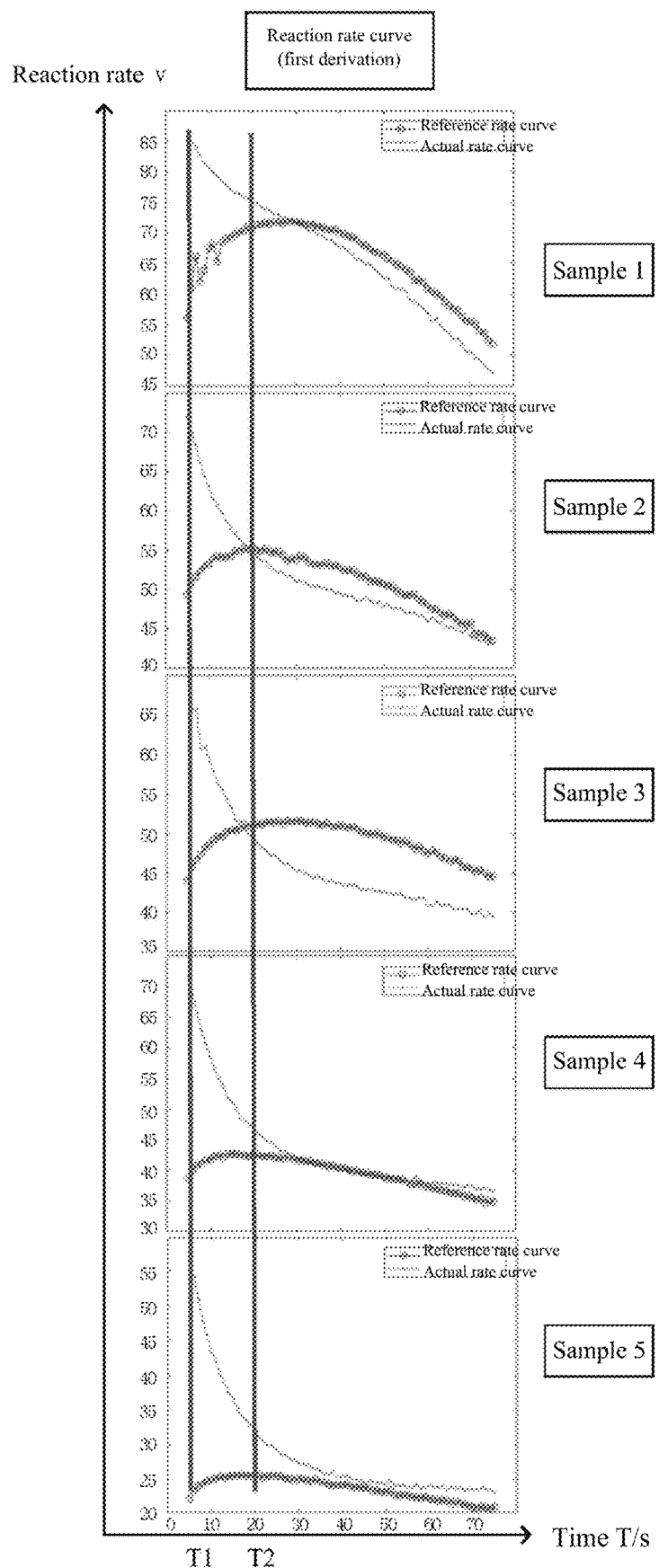
FIG. 9 is a graph showing the actual reaction rate change and the reference reaction rate change obtained by performing first derivation on the actual reaction curves obtained by testing the 5 samples of Example 1 and the corresponding reference reaction curves respectively.

First derivation was performed on the original reaction curve and the reference reaction curve obtained in Example 1 respectively to obtain an original reaction rate curve and a reference reaction rate curve (see FIG. 9).

According to the original reaction rate curve, the original reaction rate $v_1$ and $v_2$ at $T_1=5$ s and $T_2=20$ s were obtained. The mean $\overline{v}$ was calculated according to the original reaction rate per second between $T_1$ to $T_2$ (see Table 4 below).

Similarly, the reference reaction rate $v_{1(f)}$ and $v_{2(f)}$ at $T_1$ and $T_2$ were obtained after performing first derivation on the reference reaction curve. The mean $\overline{v}$ was calculated according to the reaction rate per second between $T_1$ to $T_2$ (see Table 5 below).

TABLE 4

The original reaction rate and the average reaction rate of SAA in the samples at $T_1$ and $T_2$

| | reaction rate $v_1$ at $T_1$ | reaction rate $v_2$ at $T_2$ | Average reaction rate $\overline{v}$ in $T_1$ to $T_2$ |
|---|---|---|---|
| Sample 1 | 85.33 | 75.10 | 79.41 |
| Sample 2 | 71.80 | 54.64 | 61.28 |

TABLE 4-continued

The original reaction rate and the average reaction rate of SAA in the samples at $T_1$ and $T_2$

| | reaction rate $v_1$ at $T_1$ | reaction rate $v_2$ at $T_2$ | Average reaction rate $\overline{v}$ in $T_1$ to $T_2$ |
|---|---|---|---|
| Sample 3 | 69.85 | 49.36 | 56.98 |
| Sample 4 | 71.54 | 46.61 | 56.05 |
| Sample 5 | 56.62 | 31.83 | 41.35 |

TABLE 5

The reaction rate and the average reaction rate at $T_1$ and $T_2$ on the reference reaction rate curve

| Reference curve | $T_1$ signal value $v_{1(f)}$ | $T_2$ signal value $v_{2(f)}$ | $T_1$ to $T_2$ mean $\overline{v}_{(f)}$ |
|---|---|---|---|
| Sample 1 | 56.26 | 70.56 | 66.78 |
| Sample 2 | 49.29 | 55.29 | 53.52 |
| Sample 3 | 43.96 | 51.05 | 48.97 |
| Sample 4 | 38.49 | 42.53 | 41.82 |
| Sample 5 | 22.03 | 25.57 | 24.77 |

The difference between the reaction rate of the original reaction rate curve and the reference reaction rate curve at each of $T_1$ and $T_2$ time points was calculated according to the following formula:

$$\delta v_i\% = (|v_i - v_{i(f)}|/v_{i(f)}) \times 100\%$$

$T_i = 5$ s or 20 s, when $\delta v_i\% \geq 12\%$ at one of $T_1$ and $T_2$, the presence of hook effect is determined.

Those skilled in the art can understand that it is also possible to alarm according to whether the $\delta v_i\%$ at other time points selected between $T_1$ and $T_2$, for example at 10th second or 15th second is greater than a threshold. In addition, in this example, since there are time points at which the original reaction rate curve and the reference reaction rate curve approached each other or even intersected with each other, those skilled in the art can understand that it is better to avoid selecting these time points to calculate $\delta v_i\%$. The threshold may be different when selecting different time points, and an appropriate threshold can be obtained according to the statistics of the known samples.

Alternatively, the difference between the average reaction rate of the original reaction rate curve and the average reaction rate of the reference reaction rate in 5 s-20 s was calculated according to the following formula:

$$\Delta v\% = (|\overline{v} - \overline{v}_{(f)}|/\overline{v}_{(f)}) \times 100\%$$

When $\Delta v\% \geq 12\%$, the presence of hook effect is determined.

Specific results are as shown in Table 6.

TABLE 6

Reaction rate difference at $T_1 = 5$ s and $T_2 = 20$ s and average reaction rate difference within 5-20 s

| | reaction rate difference $\delta v_1$ % at $T_1$ | reaction rate difference $\delta v_2$ % at $T_2$ | average reaction rate difference $\Delta v$ % within $T_1$ to $T_2$ |
|---|---|---|---|
| Sample 1 | 51.67% | 6.43% | 18.91% |
| Sample 2 | 49.29% | 1.18% | 14.50% |
| Sample 3 | 58.89% | 3.31% | 16.30% |
| Sample 4 | 85.87% | 9.59% | 41.82% |
| Sample 5 | 157.01% | 24.48% | 66.94% |

As can be seen from Table 6 above, the reaction rate of the sample is significantly different from the reaction rate of the reference reaction curve within the first 15 s. The reaction rate at a certain time point in the first 15 s and the reaction rate at the corresponding time point of the reference curve are compared with each other, and when there is one time point at which the difference is greater than or equal to 12%, it is determined that the sample has hook effect.

Alternatively, the average value of the reaction rate within the first 15 s of the reaction is compared with the average value of the reference curve within the corresponding time period, and when the difference is greater than 12%, it is determined that the sample has hook effect.

In addition, according to FIG. 9, the determination of hook effect can be performed by means of the contours of the reaction rate curve and the reference reaction rate curve. It can be seen from FIG. 9 that for any one of the samples 1 to 5, in a certain time period, the actual reaction rate at a later time point is always lower than the reaction rate at a previous time point, while the reference curve has a maximum value of the reaction rate in this time period.

Alternatively, in some other cases where the alarm accuracy criterion is not too high, it is also possible to simply use the original reaction rate curve to alarm. For example, starting from 0th second, the reaction rates at the later second and at the previous second are continuously compared. After a period of statistics, if the reaction rate decreases continuously over time, it can basically be determined that the sample has hook effect.

EXAMPLE 3

Figure 10:
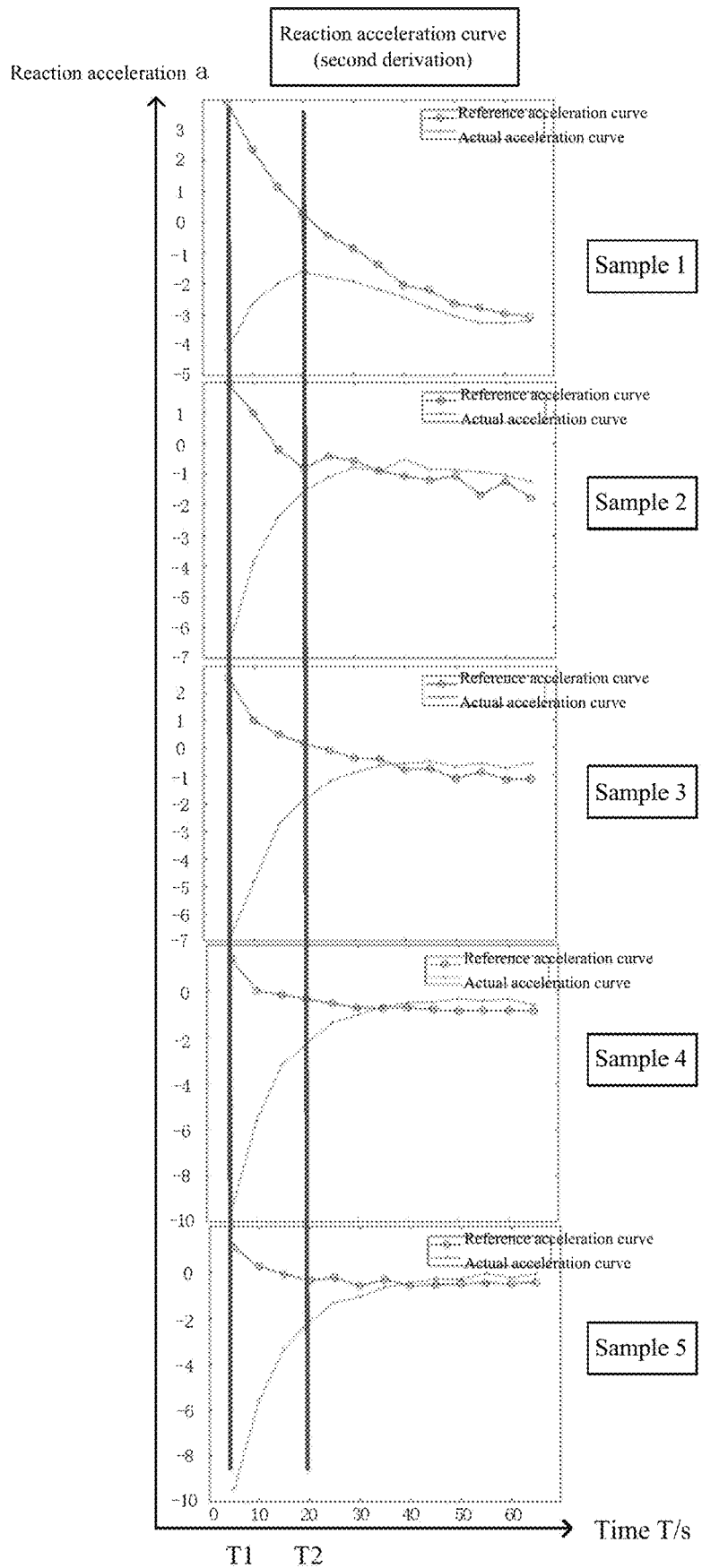
FIG. 10 is a graph showing the actual reaction acceleration change and the reference reaction acceleration change obtained by performing second derivation on the actual reaction curves obtained by testing the 5 samples of Example 1 and the corresponding reference reaction curves respectively.

Second derivative was performed on the original reaction curve and the reference reaction curve obtained in Example 1 respectively to obtain an original reaction acceleration curve and a reference reaction acceleration curve (see FIG. 10).

The original reaction accelerations $a_1$ and $a_2$ at $T_1=5$ s and $T_2=20$ s after performing the second derivation on the original measurement curve were obtained, and the mean a was calculated according to the acceleration value per second within 5th second to 20th second (see Table 7 below).

The reference reaction accelerations $a_{1(f)}$ and $a_{2(f)}$ at $T_1$ and $T_2$ after performing the second derivation on the reference reaction curve were obtained, and the mean $\bar{a}_f$ was calculated according to the acceleration value per second within 5th second to 20th second (see Table 8 below).

TABLE 7

The original reaction acceleration and the average reaction acceleration of SAA in the samples at $T_1$ and $T_2$

| | Reaction acceleration $a_1$ at $T_1$ | Reaction acceleration $a_2$ at $T_2$ | Average reaction acceleration $\bar{a}$ in $T_1$ to $T_2$ |
|---|---|---|---|
| Sample 1 | −4.17 | −1.60 | −2.60 |
| Sample 2 | −6.73 | −1.56 | −3.64 |
| Sample 3 | −6.98 | −1.84 | −4.10 |
| Sample 4 | −9.50 | −2.24 | −5.13 |
| Sample 5 | −9.49 | −2.17 | −5.14 |

TABLE 8

The reaction acceleration and the average reaction acceleration at $T_1$ and $T_2$ on the reference reaction acceleration curve

| Reference curve | Reaction acceleration $a_{1(f)}$ at $T_1$ | Reaction acceleration $a_{2(f)}$ at $T_2$ | Average reaction acceleration $\bar{a}_{(f)}$ in $T_1$ to $T_2$ |
|---|---|---|---|
| Sample 1 | 3.89 | 0.24 | 1.91 |
| Sample 2 | 1.98 | −0.82 | 0.48 |
| Sample 3 | 2.53 | 0.16 | 1.04 |
| Sample 4 | 1.40 | −0.35 | 0.23 |
| Sample 5 | 1.04 | −0.36 | 0.20 |

The difference between the reaction accelerations at time points $T_1$ and $T_2$ was calculated according to the following formula:

$$\delta a_i \% = |(a_i - a_{i(f)})/a_{i(f)}| \times 100\%$$

$T_i=5$ or 20 s, when $\delta a_i \% > 80\%$ at one of $T_1$ and $T_2$, the presence of hook effect is determined. Similarly, it is also possible to alarm according to whether the $\delta a_i \%$ at other time points selected between $T_1$ and $T_2$, for example at 10th second or 15th second is greater than a threshold. In addition, in this example, since there were time points at which the original reaction acceleration curve and the reference reaction acceleration curve approached each other or even intersected with each other, those skilled in the art should understand that it is better to avoid selecting these time points to calculate $\delta a_i \%$. The threshold may be different when selecting different time points, and an appropriate threshold can be obtained according to the statistics of the known samples.

And the difference between the measurement means within 5 s-20 s was calculated according to the following formula:

$$\Delta a \% = |(\bar{a} - \bar{a}_{(f)})/\bar{a}_{(f)}| \times 100\%$$

When $\Delta a \% \geq 80\%$, the presence of hook effect is determined.

Specific results are as shown in Table 9.

TABLE 9

The difference of reaction acceleration at 0th s or 15th s and the difference of average reaction acceleration within 5-20 s

| | Difference $\delta a_1 \%$ at $T_1$ | Difference $\delta a_2 \%$ at $T_2$ | Difference of the mean $\Delta a \%$ within $T_1$ to $T_2$ |
|---|---|---|---|
| Sample 1 | 207.20% | 766.67% | 236.13% |
| Sample 2 | 439.90% | 90.24% | 858.33% |
| Sample 3 | 375.89% | 1250.00% | 494.23% |
| Sample 4 | 778.57% | 540.00% | 2330.43% |
| Sample 5 | 1012.50% | 502.78% | 2670.00% |

As can be seen from Table 9 above, the reaction acceleration of the sample is very different from the reference reaction acceleration in the first 15 s. The difference between the reaction acceleration at a certain time point within the first 15 s and the reaction acceleration at the corresponding time point of the reference curve is compared, and when the difference is greater than or equal to 80%, it is determined that the sample has hook effect.

Alternatively, the average value of the reaction acceleration within the first 15 s of the reaction is compared with the average value of the reference curve within the corresponding time period, and when the difference is greater than 80%, it is determined that the sample has hook effect.

In addition, according to FIG. 10, the determination of hook effect can be performed by means of the contours of the original reaction acceleration curve and the reference reaction acceleration curve. It can be seen from FIG. 10 that for any one of the samples 1 to 5, on the actual reaction acceleration curve, the reaction acceleration at a later time point is always greater than the reaction acceleration at a previous time point, while on the reference curve, the reaction acceleration at a later time point is always smaller than the reaction acceleration at a previous time point. Therefore, it is determined that the sample has hook effect.

Alternatively, in some other cases where the alarm accuracy criterion is not too high, it is also possible to simply use the original reaction acceleration curve to alarm. For example, starting from 0th second, the reaction accelerations at the later second and the previous second are continuously compared. After a period of statistics, if the reaction acceleration increases continuously over time, it can basically be determined that the sample has hook effect.

The foregoing description merely relates to the preferred embodiments of the disclosure, and is not intended to limit the scope of patent of the disclosure. All equivalent variations made by using the content of the specification and the accompanying drawings of the disclosure from the concept of the disclosure, or the direct/indirect applications of the contents in other related technical fields all fall within the scope of patent protection of the disclosure.

What is claimed is:

1. A method of detecting hook effect in turbidimetric inhibition immunoassay, comprising:
   a) after a sample is mixed with a reaction reagent so that an analyte in the sample starts to react, obtaining an actual measured value $A_i$ at a time point $T_i$ within a predetermined time period $T_1$ to $T_n$ after the reaction starts, where i is an integer from 1 to n, so that a plurality of actual measured values $A_1$ to $A_n$ are obtained to generate an actual reaction curve for the predetermined time period;
   b) estimating a concentration $C_e$ of the analyte based on the actual reaction curve;
   c) obtaining, according to the estimated concentration $C_e$ of the analyte, a pre-stored reference reaction curve corresponding to the estimated concentration; and
   d) comparing distribution information of the actual reaction curve for the predetermined time period with distribution information of the reference reaction curve for the corresponding time period, to determine whether the sample has hook effect.

2. The method of claim 1, wherein in step a), $T_n$ is smaller than or equal to a time point $T_{90}$ at which the reaction proceeds to 90% or 70% or 50% of an entire reaction time; or
   wherein in step a), $T_n$ is smaller than or equal to a corresponding time point at which a slope trend of the reference reaction curve changes.

3. The method according to claim 1, wherein the predetermined time period accounts for 10% to 70%, or 15% to 50%, or 15% to 40% of an entire reaction time; or
   wherein the predetermined time period for generating the actual reaction curve of the analyte is a time period from start of the reaction to completion of 10% to 70%, or 10% to 50%, or 10% to 40% of the reaction.

4. The method of claim 1, wherein the distribution information comprises at least one of a measured value feature, a reaction rate feature, and a reaction acceleration feature.

5. The method of claim 1, wherein step d) comprises:
   comparing the actual measured values of the actual reaction curve for the predetermined time period with reference values of the reference reaction curve for the corresponding time period; or
   performing first derivation on the actual reaction curve and the reference reaction curve respectively to obtain an actual reaction rate curve and a reference reaction rate curve, and comparing the actual reaction rate curve with the reference reaction rate curve; or
   performing second derivation on the actual reaction curve and the reference reaction curve respectively to obtain an actual reaction acceleration curve and a reference reaction acceleration curve, and comparing the actual reaction acceleration curve with the reference reaction acceleration curve; or
   comparing values of respective distribution information of the actual reaction curve and the reference reaction curve at a same reaction time point, and/or comparing average values of a plurality of respective distribution information of the actual reaction curve and the reference reaction curve within a same time period.

6. The method of claim 1, wherein in step d), the actual measured value $A_i$ of the actual reaction curve at the time point $T_i$ and a reference value $A_{i(f)}$ of the reference reaction curve at a corresponding time point are substituted into the following formula to obtain a reaction difference $\delta_i$ %:

$$\delta_i \% = [(A_i - A_{i(f)})/A_{i(f)}] \times 100\%$$

when $\delta_i$ % is greater than or equal to a predetermined threshold, it is determined that the sample has hook effect, and/or an average measured value $\overline{A}$ of the actual reaction curve within the time period $T_1$ to $T_n$ and an average reference value $\overline{A}_{(f)}$ the reference reaction curve within the corresponding time period are substituted into the following formula to obtain an average reaction difference 4% within the time period:

$$\Delta \% = [(\overline{A} - \overline{A}_{(f)})/\overline{A}_{(f)}] \times 100\%$$

when $\Delta$ % is greater than or equal to a predetermined threshold, it is determined that the sample has hook effect.

7. The method of claim 1, wherein step d) comprises:
performing first derivation on the actual reaction curve $A=f(T)$ and the reference reaction curve $A_{(f)}=f(T_{(f)})$ respectively with respect to time to obtain an actual reaction rate curve as a function of time $v=A'=f'(T)$ and a reference reaction rate curve as a function of time $v'=A_{(f)}'=f'(T_{(f)})$; and
a reaction rate value $v_i$ at the time point $T_i$ and a reference reaction rate value $v_{i(f)}$ at a corresponding time point are substituted into the following formula to obtain a reaction rate difference $\delta v_i$ %:

$$\delta v_i \% = (|v_i - v_{i(f)}|/v_{i(f)}) \times 100\%$$

when $\Delta v_i$ % is greater than or equal to a predetermined threshold, it is determined that the sample has hook effect, and/or an average reaction rate value $\overline{v}$ within the time period $T_1$ to $T_n$ and an average reference reaction rate value $\overline{v}_{(f)}$ within the corresponding time period are substituted into the following formula to obtain an average reaction rate difference $\Delta v$ % within the time period:

$$\Delta v \% = (|\overline{v} - \overline{v}_{(f)}|/\overline{v}_{(f)}) \times 100\%$$

when $\Delta v$ % is greater than or equal to a predetermined threshold, it is determined that the sample has hook effect.

8. The method of claim 7, wherein $T_n$ is smaller than or equal to a corresponding time point at which the difference $\delta v_i$ % is zero.

9. The method of claim 1, wherein step d) comprises:
performing second derivation on the actual reaction curve $A=f(T)$ and the reference reaction curve $A_{(f)}=f(T_{(f)})$ respectively to obtain an actual reaction acceleration curve as a function of time $a=A''=f''(T)$ and a reference reaction acceleration curve as a function of time $a_f=A_{(f)}''=f''(T_{(f)})$; and a reaction acceleration value $a_i$ at the time point $T_i$ and a reference reaction acceleration value $a_{i(f)}$ at a corresponding time point are substituted into the following formula to obtain a reaction acceleration difference $\delta a_i$ %:

$$\delta a_i \% = |(a_i - a_{i(f)})/a_{i(f)}| \times 100\%$$

when $\delta a_i$ % is greater than or equal to a predetermined threshold, it is determined that the sample has hook effect,
and/or
an average reaction acceleration value $\bar{a}$ within the time period $T_1$ to $T_n$ and an average reference reaction acceleration value $\bar{a}_{(f)}$ within the corresponding time period are substituted into the following formula to obtain an average reaction acceleration difference $\Delta a$ % within the time period:

$$\Delta a \% = |(\bar{a} - \bar{a}_{(f)})/\bar{a}_{(f)}| \times 100\%$$

when $\Delta a$ % is greater than or equal to a predetermined threshold, it is determined that the sample has hook effect.

10. The method of claim 9, wherein $T_n$ is smaller than or equal to a time point at which the reference reaction acceleration reaches a substantially constant $a_{const(f)}$.

11. The method of claim 1, wherein step d) comprises:
performing first derivation on the actual reaction curve $A=f(T)$ and the reference reaction curve $A_{(f)}=f(T_{(f)})$ respectively with respect to time to obtain an actual reaction rate curve as a function of time $v=A'=f'(T)$ and a reference reaction rate curve as a function of time $v'=A_{(f)}'=f'(T_{(f)})$; and it is determined that the sample has hook effect, when the actual reaction rate curve $v=A'=f'(T)$ has an overall trend that the actual reaction rate decreases over time within the time period of $T_1$ to $T_n$, and the reference reaction rate curve $v'=A_{(f)}'=f'(T_{(f)})$ has an overall trend that the reference reaction rate increases first and then decreases over time within the corresponding time period;
or
wherein step d) comprises:
performing second derivation on the actual reaction curve $A=f(T)$ and the reaction reference curve $A_{(f)}=f(T_{(f)})$ respectively to obtain an actual reaction acceleration curve as a function of time $a=A''=f''(T)$ and a reference reaction acceleration curve as a function of time $a_{(f)}=A_{(f)}''=f''(T_{(f)})$; and it is determined that the sample has hook effect, when within the time period of $T_1$ to $T_n$, the actual reaction acceleration curve $a=A''=f''(T)$ has an overall trend that the actual reaction acceleration increases over time and the reference reaction acceleration curve $a_{(f)}=A_{(f)}''=f''(T_{(f)})$ has an overall trend that the reference reaction acceleration decreases over time.

12. The method of claim 1, wherein the sample is a human whole blood sample, and the analyte in the sample is C-reactive protein or serum amyloid A protein.

13. A method for detecting hook effect in turbidimetric inhibition immunoassay, wherein the method comprises:
a) after a sample is mixed with a reaction reagent so that an analyte in the sample starts to react, obtaining a measured value $A_i$ at a time point $T_i$ within a predetermined time period $T_1$ to $T_n$ after the reaction starts, where i is an integer from 1 to n, so that a plurality of measured values $A_1$ to $A_n$ are obtained to generate a reaction curve for the time period; and
b) performing derivation on the reaction curve $A=f(T)$ within the predetermined time period with respect to time T, to obtain a derivative curve, and determining whether the sample has hook effect according to a contour of the derivative curve.

14. The method of claim 13, wherein in step b), first derivation is performed on the reaction curve $A=f(T)$ with respect to time T to obtain a reaction rate curve as a function of time $v=A'=f'(T)$, and
it is determined that the sample has hook effect when the reaction rate curve $v=A'=f'(T)$ has an overall trend that the reaction rate decreases over time within the time period of $T_1$ to $T_n$;
or
wherein in step b), second derivation is performed on the reaction curve $A=f(T)$ with respect to time T to obtain a reaction acceleration curve as a function of time $a=A''=f''(T)$, and
it is determined that the sample has hook effect when the reaction acceleration curve $a=A''=f''(T)$ has an overall trend that the reaction acceleration increases over time within the time period of $T_1$ to $T_n$.

15. The method of claim 13, wherein the sample is a human whole blood sample, and the analyte in the sample is C-reactive protein or serum amyloid A protein.

16. A blood analysis system, comprising:
a sampling portion configured to obtain a blood sample and transfer the blood sample to a reaction portion;
a reagent supply portion configured to store a first reaction reagent and supply the first reaction reagent to the reaction portion as needed;
the reaction portion comprising a first reaction chamber and configured to mix the blood sample with the first reaction reagent to prepare a first test solution;
a detection system comprising a light source and a detector for testing the first test solution and configured to obtain measured values of the test solution;
a controller, which is coupled to the sampling portion, the reagent supply portion, the reaction portion, and the detection system, and is configured to control actions of the sampling portion, the reagent supply portion, the reaction portion, and the detection system; and
a processor, which is coupled to the detection system, wherein
the processor is configured to: obtain, from the detection system, a measured value $A_i$ at a time point $T_i$ within a predetermined time period $T_1$ to $T_n$ after the reaction starts, where i is an integer from 1 to n, so that a plurality of measured values $A_1$ to $A_n$ are obtained to generate an actual reaction curve for the time period; estimate a concentration $C_e$ of the analyte based on the actual reaction curve and a pre-stored calibration curve; obtain a pre-stored reference reaction curve corresponding to the estimated concentration according to the estimated concentration $C_e$ of the analyte; and compare distribution information of the actual reaction curve for the predetermined time period with distribution information of the reference reaction curve for the corresponding time period, to determine whether the sample has hook effect, alternatively, the processor is configured to: obtain, from the detection system, a measured value $A_i$ at a time point $T_i$ within a time period $T_1$ to $T_n$ after the reaction starts, where i is an integer from 1 to n, so that a plurality of measured values $A_1$ to $A_n$ are obtained to generate a reaction curve for the time period; and perform derivation on the reaction curve $A=f(T)$ within the time period with respect to time T, to obtain a derivative curve, and determine whether the sample has hook effect based on a contour of the derivative curve, and output a determination result to the controller.

17. The blood analysis system of claim 16, wherein the controller is further configured to:

control the detection system to stop testing when receiving a result that the current test sample has hook effect;

control the sampling portion to obtain the sample again and transfer the obtained sample to the first reaction chamber of the reaction portion;

control the reagent supply portion to supply the first reaction reagent to the first reaction chamber to prepare a second test solution, wherein a dilution factor of the sample in the second test solution is greater than a dilution factor of the sample in the first test solution; and control the detection system to test the second test solution.

18. The blood analysis system of claim 16, wherein the sample is a whole blood sample, and the first reagent comprises a hemolytic agent for lysing red blood cells in the sample and a latex reagent for performing turbidimetric inhibition immunoreaction with the analyte in the sample.

19. The blood analysis system of claim 16, further comprising a second detection system, and the reaction portion further comprises a second reaction chamber; the second detection system comprises a light source, a flow chamber for cells to pass in line one by one, a liquid circuit system, and a second detector;

the controller is further configured to: control the sampling portion to divide the sample into two parts, and respectively transfer to the first reaction chamber and the second reaction chamber; control the reagent supply portion to transfer a second reagent to the second reaction chamber, wherein the sample reacts with the second reagent in the second reaction chamber to obtain a third test solution; control the second detection system, wherein the third test solution is transferred to the flow chamber under the driving of the liquid circuit system, the light source illuminates the flow chamber, and the second detector collects scattered light signals generated by the cells; and the processor is further configured to obtain the scattered light signals, and classify white blood cells in the sample into at least three types of lymphocytes, monocytes, and neutrophils according to the scattered light signals.

20. The blood analysis system of claim 16, wherein $T_n$ is smaller than or equal to a time point $T_{90}$ at which the reaction proceeds to 90% or 70% or 50% of an entire reaction time; or $T_n$ is smaller than or equal to a corresponding time point at which a slope trend of the reference curve changes.

* * * * *